US008670115B2

(12) United States Patent
Miyoshi et al.

(10) Patent No.: US 8,670,115 B2
(45) Date of Patent: Mar. 11, 2014

(54) INSPECTION METHOD AND INSPECTION APPARATUS

(75) Inventors: Yuji Miyoshi, Hitachinaka (JP); Kazuhisa Hasumi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 273 days.

(21) Appl. No.: 13/141,737

(22) PCT Filed: Dec. 14, 2009

(86) PCT No.: PCT/JP2009/006829
§ 371 (c)(1),
(2), (4) Date: Jun. 23, 2011

(87) PCT Pub. No.: WO2010/073527
PCT Pub. Date: Jul. 1, 2010

(65) Prior Publication Data
US 2011/0255080 A1    Oct. 20, 2011

(30) Foreign Application Priority Data

Dec. 26, 2008   (JP) ................................. 2008-331840

(51) Int. Cl.
*G01N 21/00*   (2006.01)
(52) U.S. Cl.
USPC ..................................................... 356/237.1
(58) Field of Classification Search
None
See application file for complete search history.

(56) References Cited

U.S. PATENT DOCUMENTS

2004/0130727 A1*   7/2004   Isozaki et al. ................. 356/504

FOREIGN PATENT DOCUMENTS

| JP | 4-109108 A | 4/1992 |
| JP | 7-43310 A | 2/1995 |
| JP | 2003-185588 A | 7/2003 |
| JP | 2006-261327 A | 9/2006 |
| JP | 2008-032600 A | 2/2008 |

\* cited by examiner

*Primary Examiner* — Gregory J Toatley
*Assistant Examiner* — Amanda Merlino
(74) *Attorney, Agent, or Firm* — Miles & Stockbridge P.C.

(57) ABSTRACT

The inspection conditions of a known inspection apparatus necessary for inspection are such that wafers are individually prepared for respective layer types and layer thicknesses, and standard particles having different sizes are applied to all of the wafers. Moreover, the wafers to which standard particles have been applied and which have been prepared for the respective layer types and layer thicknesses are inspected by the inspection apparatus to determine the optimal inspection conditions for the respective layer types and layer thicknesses. Therefore, there are problems that it requires long time and involves high cost to determine the inspection conditions. In the invention, the relation between the layer thickness and the scattering intensity in the inspection apparatus is calculated. The scattering intensity is divided into a plurality of intensity regions, and the inspection conditions optimized for the respective divided regions are determined. The inspection conditions are shared in each divided intensity region, whereby the time and cost necessary to determine the inspection conditions can be dramatically reduced.

18 Claims, 18 Drawing Sheets

FIG. 13

| RECIPE NAME | LAYER TYPE | LAYER THICKNESS | POLARIZATION CONDITION | MEASURED RANGE | GENERATED DAY AND TIME |
|---|---|---|---|---|---|
| RECIPE A | LAYER TYPE A | 300nm | POLARIZATION CONDITION A | 100~500nm | 2009/7/6 15:00 |
| RECIPE B | LAYER TYPE B | 550nm | POLARIZATION CONDITION A | 100~500nm | 2009/7/6 15:00 |
| RECIPE C | LAYER TYPE C | 180nm | POLARIZATION CONDITION B | 150~500nm | 2009/7/6 15:00 |
| RECIPE D | LAYER TYPE D | 100nm | POLARIZATION CONDITION B | 300~1000nm | 2009/7/6 15:00 |
| RECIPE E | LAYER TYPE E | 50nm | POLARIZATION CONDITION B | 300~1000nm | 2009/7/6 15:00 |
| RECIPE F | LAYER TYPE F | 380nm | POLARIZATION CONDITION A | 90~500nm | 2009/7/7 15:00 |

RECIPE SELECTION

RECIPE HOLDER SELECTION — 1302

1301

OK — 1303   Cancel — 1304

FIG. 15

| LAYER TYPE | REFRACTIVE INDEX n | REFRACTIVE INDEX k | LAYER THICKNESS(nm) | POLARIZATION | PARTICLE SIZE(nm) |
|---|---|---|---|---|---|
| LAYER TYPE A | 1.000 | 0.000 | 0~1000 | POLARIZATION CONDITION A,C | 40~1000 |
| LAYER TYPE B | 2.000 | 0.000 | 0~300 | POLARIZATION CONDITION A,C | 40~1000 |
| LAYER TYPE C | 1.500 | 3.000 | 0~500 | POLARIZATION CONDITION A,B,C | 40~1000 |
| LAYER TYPE D | 3.000 | 3.000 | 0~300 | POLARIZATION CONDITION B | 40~1000 |
| LAYER TYPE E | 1.600 | 0.000 | 0~300 | POLARIZATION CONDITION B | 40~1000 |
| LAYER TYPE F | 1.400 | 0.000 | 0~1000 | POLARIZATION CONDITION A,C | 40~1000 |

SIMULATION DATA LIST

1501 — TARGETED APPARATUS: ▼ APPARATUS A

1601 INSPECTION CONDITION — INSPECTION PARAMETER A, LOW ANGLE PMT: PMT CONDITION A
1605 INSPECTION PARAMETER B, HIGH ANGLE PMT: PMT CONDITION B
INSPECTION PARAMETER C
INSPECTION PARAMETER D

1602
1606 RECIPE NAME: INSPECTION CONDITION C
1607 SENSITIVITY CURVE NAME: LOW: SENSITIVITY CURVE C  HIGH: SENSITIVITY CURVE D — 1608

1603 AD VALUE SETTING   1611 INSPECTION CONDITION UPDATE    CH SETTING — 1604

| LOW ANGLE | | HIGH ANGLE | |
|---|---|---|---|
| PSL(nm) | AD VALUE | PSL(nm) | AD VALUE |
| 41 | 1 | 41 | 1 |
| 50 | 1 | 50 | 1 |
| 61 | 1 | 61 | 1 |
| 73 | 1 | 73 | 1 |
| 81 | 6 | 81 | 6 |
| 92 | 40 | 92 | 1 |
| 97 | 54 | 97 | 1 |
| 102 | 68 | 102 | 1 |
| 126 | 124 | 126 | 1 |
| 152 | 171 | 152 | 22 |
| 199 | 236 | 199 | 54 |
| 299 | 256 | 299 | 103 |
| 499 | 256 | 499 | 225 |
| THRESHOLD VALUE | 51 | | 49 |

1609 / 1610

| | LOW ANGLE | | HIGH ANGLE | |
|---|---|---|---|---|
| | AD VALUE | Size | AD VALUE | Size |
| CH1 | 58 | 0.10 | 50 | 0.30 |
| CH2 | 168 | 0.15 | 84 | 0.35 |
| CH3 | 240 | 0.20 | 128 | 0.40 |
| CH4 | 320 | 0.25 | 235 | 0.50 |
| CH5 | 355 | 0.30 | | |
| CH6 | 417 | 0.35 | | |
| CH7 | 450 | 0.40 | | |
| CH8 | 498 | 0.50 | | |

1612 / 1613

[RECIPE OUTPUT] 1614   [SENSITIVITY CURVE OUTPUT] 1615   [Cancel] 1616 ated from between particle size and scattering intensity, also serves as a calibration curve.

INSPECTION METHOD AND INSPECTION APPARATUS

TECHNICAL FIELD

The present invention relates to an inspection method and an inspection apparatus for inspecting defects, for example, to a technique for inspecting the defects by using a generating method of an inspection condition and this inspection condition, which is desirably used for a semiconductor device inspection/measurement and a semiconductor manufacturing process management in the field of semiconductor device manufacture.

BACKGROUND ART

For example, in the semiconductor manufacturing process, a foreign substance on a wafer surface as a substrate and a pattern defect cause inferior products. For this reason, it is preferred that a monitor is implemented at all times of whether a problem is present in manufacturing devices and manufacturing environment, and the inspection apparatus has been used so that the defects, such as the foreign substance, pattern defect, appearance defect, etc., are detected to make them quantitative. It is also necessary to confirm whether the defect gives the product a fatal effect, by observing a defect shape etc. with use of an observing device.

In the past, the inspection condition necessary for inspecting the inspection apparatus has been provided such that a wafer is prepared for every layer type and layer thickness, formed on a substrate, standard particles of plural sizes are applied to all of the wafers, the wafers for every layer type and layer thickness, applied with the standard particles are inspected by the inspection apparatus, and an optimal inspection condition is generated for every layer type and layer thickness. For this reason, it has taken a great period of time and cost to generate the inspection condition for every layer type and layer thickness.

In recent years, the type of semiconductor device has rapidly increased with the case where the semiconductor devises are currently diversified. A frequency of generating the number of inspection condition and the inspection condition necessary for inspecting the defect, has also increased rapidly. Further, since the inspection condition has been subjected to a complicated effect due to a defect inspection apparatus having high performance, the cost and time necessary for generating the inspection condition of the defect inspection apparatus are increased more and more. Therefore, it has been demanded to reduce an operation of generating the inspection condition in the defect inspection apparatus. For example, a patent literature 1 discloses an inspection system for a purpose of acquiring efficiency for an inspection time and a manufacturing method of a semiconductor device, by using a classification of wafer lots and a feedback to a recipe.

CITATION LIST

Patent Literature

PATENT LITERATURE 1: JP-A-2006-261327

SUMMARY OF INVENTION

Technical Problem

In the past, the inspection condition necessary for inspecting the inspection apparatus has been provided such that the wafer is prepared for every layer type and layer thickness, formed on a substrate, and standard particles of plural sizes are applied to all of the wafers. Further, the wafers applied with the standard particles for every layer type and layer thickness have been inspected by the inspection apparatus, and the optimal inspection condition has been generated for every layer type and layer thickness. In consequence, it has taken a great period of time and a material/cost to generate the inspection condition, therefore, there has been a problem to reduce them.

An object of the invention is to reduce an operation time for generating the inspection condition.

Solution to Problem

A first aspect of the invention is that a variation width of a scattering intensity is divided into plural regions as classified by an intensity on the basis of a relation between the layer thickness of layer formed on the substrate and the scattering intensity.

The aspects other than the above-mentioned aspect are described below, for example.

A second aspect of the invention is that the variation width of the scattering intensity is transformed to a size by using a sensitivity curve acquired from a relation between a particle size and the scattering intensity. In addition, the sensitivity curve acquired from the relation between the particle size and scattering intensity is sometimes referred to as a calibration curve.

A third aspect of the invention is that the variation width of scattering intensity is divided into plural numbers on the basis of number of division of either the variation width after divided or the scattering intensity variation width.

A fourth aspect of the invention is that the inspection condition is shared for every divided scattering intensity region to inspect by the shared inspection condition.

A fifth aspect of the invention is that the inspection condition suitable to an inspection targeted substrate is selected from among the inspection requests shared for every divided scattering intensity region to then inspect.

A sixth aspect of the invention is that the layer thickness is displayed necessary for generating the inspection condition to be shared for every divided scattering intensity region.

A seventh aspect of the invention is that the inspection apparatus has a database coupled to the inspection apparatus and a simulator coupled to the database.

An eighth aspect of the invention is that the scattering intensity corresponding to the particle size is calculated by using simulation data and actual measured data.

A ninth aspect of the invention is that the scattering intensity corresponding to the calculated particle size and the inspection condition for use in the inspection are calculated by using the inspection condition to be a reference, corresponding simulation data and actual measured data.

A tenth aspect of the invention is that a simulated result is corrected by using a refractive index to calculate the scattering intensity corresponding to the particle size.

An eleventh aspect of the invention is that a correction coefficient acquired from a compared result of an actual measured value and a simulated value is reflected to a calculating expression for the scattering intensity to calculate the scattering intensity corresponding to the particle size.

A twelfth aspect of the invention is that a control unit in the inspection apparatus is controlled on the basis of a signal from the database.

Advantageous Effects of Invention

According to one aspect of the invention, the operation time for generating the inspection condition can be reduced.

BRIEF DESCRIPTION OF DRAWINGS

FIG. 13 is a recipe selection screen in the embodiment of the invention;

FIG. 15 is a recipe output setting screen in the embodiment of the invention;

FIG. 16 is a simulation data list display screen in the embodiment of the invention;

DESCRIPTION OF EMBODIMENTS

In the past, an inspection condition necessary for an inspection of an optical wafer surface inspection apparatus for inspecting foreign substances and defects on a wafer surface has been provided such that wafers are prepared for every layer type and layer thickness, standard particles are applied to these wafers, the wafers are inspected by an inspection apparatus, an optimal inspection condition is generated for every layer type and layer thickness, etc. Therefore, it has taken a great period of time and cost. A generation for a new inspection condition has also been required for when the layer type and layer thickness of the inspection targeted wafer are changed due to a reason of changing a manufacturing process etc. The invention is applied to the optical wafer surface inspection apparatus. To this end, a scattering intensity characteristic regarding the layer thickness is calculated by a simulator etc., a calculated result is divided into plurality as classified by the scattering intensity, and the inspection condition is generated for every divided region to make it shared. In consequence, an operation of generating the inspection condition is reduced.

Hereinafter, one embodiment of the invention will be described with reference to the drawings.

Figure 1:
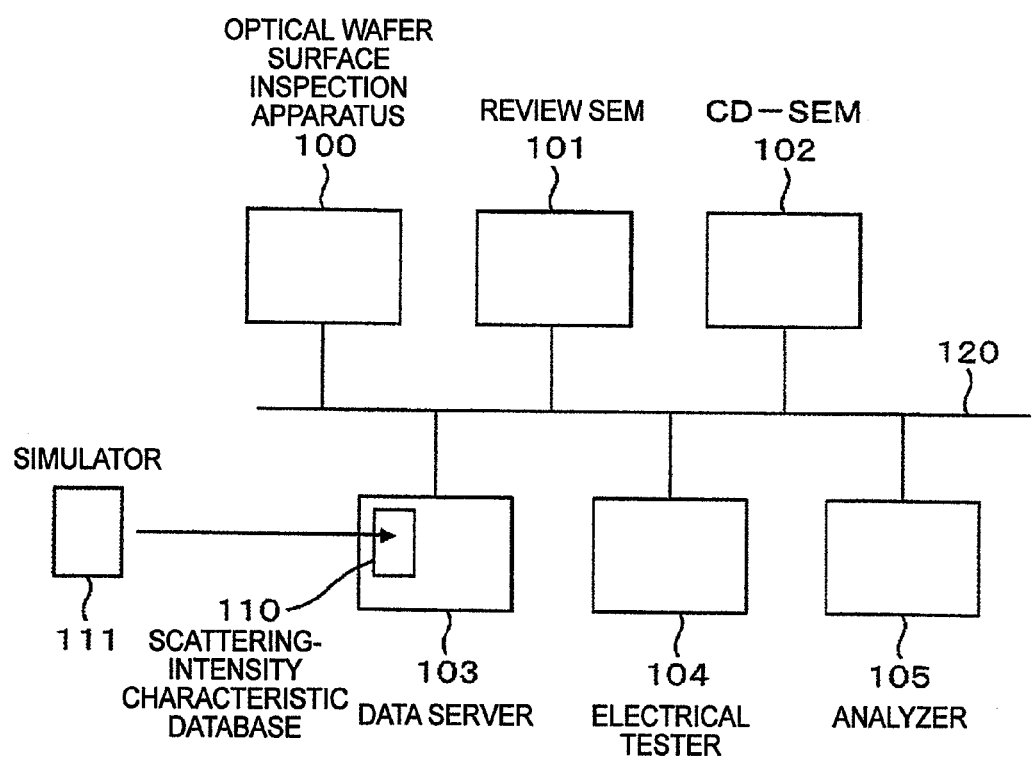
FIG. 1 is a system configuration diagram of a first embodiment.

FIG. 1 shows an embodiment example of a system regarding the invention. The system is configured by including an optical wafer surface inspection apparatus 100, a review SEM (Scanning Electron Microscope) 101, a CD-SEM (Critical Dimension-Scanning Electron Microscope) 102, a data server 103, an electrical tester 104 and an analyzer 105. Each of the devices is coupled with a network 120. The data server 103 is a computer to be able to store measured data, acquired by the devices, including the foreign substance and a defect inspected result acquired by the optical wafer surface inspection apparatus 100, test data acquired from the electrical tester 104, etc.

The data server 103 has a scattering intensity characteristic database 110 to store the scattering intensity characteristic regarding the layer thickness for every layer type calculated by a simulator 111.

Figure 2:
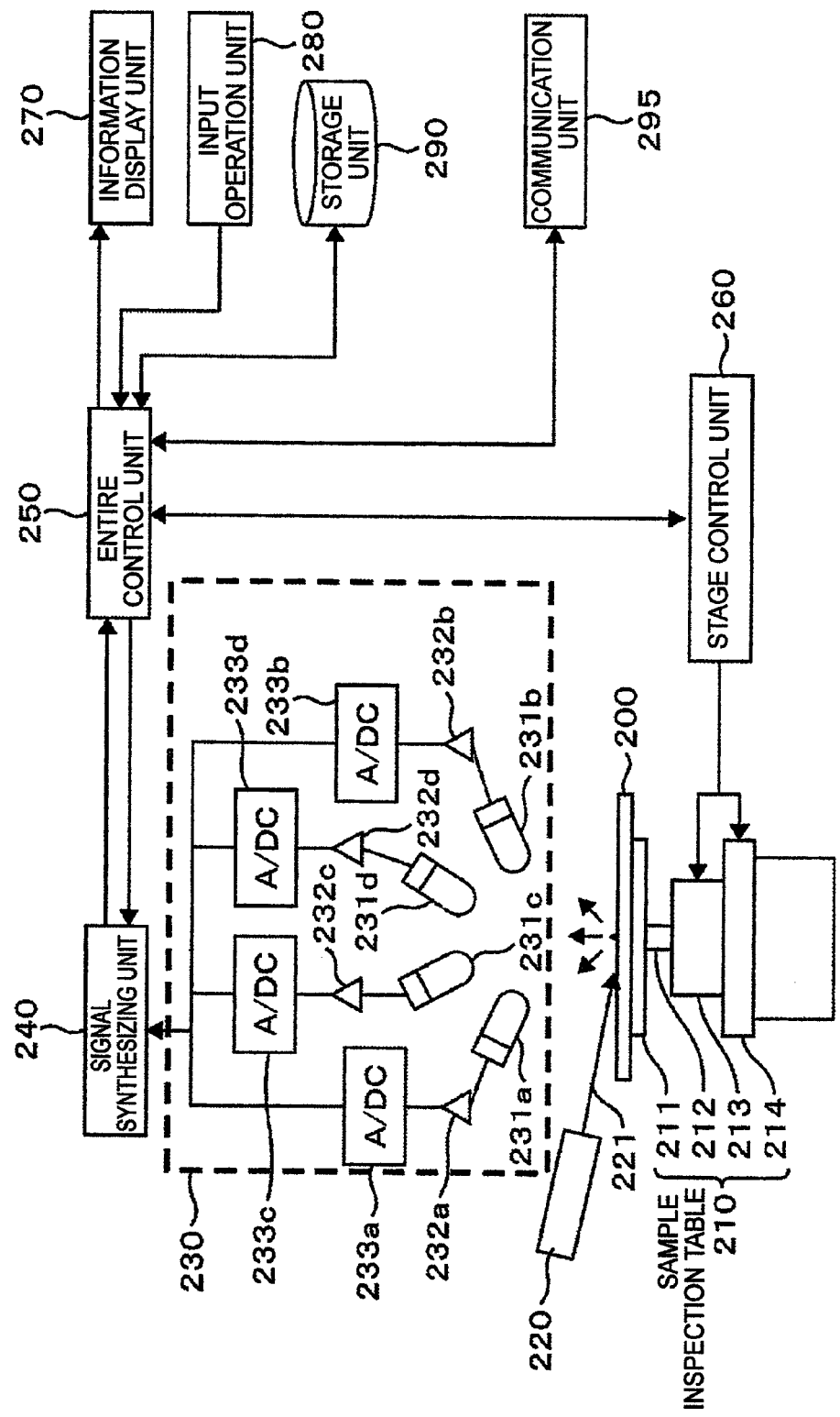
FIG. 2 is a configuration diagram of an optical wafer surface inspection apparatus in the first embodiment of embodiments in the invention.

FIG. 2 is a configuration diagram of the optical wafer surface inspection apparatus. The optical wafer surface inspection apparatus 100 is configured by a sample inspection table 210, an illumination light source 220, a scattering light detecting unit 230, a signal synthesizing unit 240, an entire control unit 250, a stage control unit 260, an information display unit 270, an input operation unit 280, a storage unit 290 and a communication unit 295.

The sample inspection table 210 provides a sample stage 211 on which a wafer 200 etc. is loaded, a rotation drive unit 213 for rotating the sample stage 211 about a rotation axis 212 and a slide drive unit 214 for moving the sample stage 211 in a radial direction.

Here, the rotation drive unit 213 and slide drive unit 214 are controlled by the after-mentioned stage control unit 260 received an instruction signal from the after-mentioned entire control unit 250.

The illumination light source 220 is installed such that a light (illumination light 221) to be irradiated is irradiated on a certain point (spot) on the sample stage 211. For this reason, the slide drive unit 214 moves in the radial direction while the rotation drive unit 213 on the sample inspection table 210 rotates about the rotation axis 212 by the control of stage control unit 260, so that all of locations on the sample stage 211 can be made spots and the illumination light 221 can be irradiated on a specific position of the wafer 200 loaded on the sample stage 211.

The specific position on the wafer 200 irradiated by the illumination light 221 can be coordinated in X and Y in the stage control unit 260 by using a rotated angle from the rotation drive unit 213 and a moved distance in the radial direction from the slide drive unit 214. The acquired data coordinated in X and Y is stored in the storage unit 290 via the entire control unit 250.

Here, it is desirable that the illumination light 221 is a high focusing performance light like a laser beam so that an area on which the light is irradiated makes as small as possible.

The scattering light detecting unit 230 has detectors 231a to 231d for detecting the light. FIG. 2 shows the total four detectors: the detectors 231a, 231d arranged on a low angle position and the detectors 231b, 231c arranged on a high angle position. This is not however limited to the number of detectors. In the detectors 231a to 231d, more than two detectors may be arranged such that at least either an azimuth or an elevation between the spots and the detectors becomes different. The detectors 231a to 231d detect respectively scattering lights generated from the spot by irradiating the illumination light (laser light) 221 on the surface of wafer 200 from the illumination light source 220. A detected signal output from the detectors 231a to 231d contains a signal (defect signal) of the foreign substance and defect and a surface roughness signal (Haze signal).

In the scattering light detecting unit 230, the detectors 231a to 231d are coupled respectively with amplifiers 232a to 232a and subsequently coupled respectively with A/D converters 233a to 233d. In this way, the detected signals from the detectors 231a to 231d are amplified respectively by amplifiers 232a to 232d and digitalized respectively by the A/D converters 233a to 233d.

The signal synthesizing unit 240 generates a synthesized signal synthesized with the digitalized detected signals of the detectors 231a to 231d in accordance with a specified operation condition (program). The data of synthesized signal synthesized in the signal synthesizing unit 240 and of the digitalized detected signals, originated for the synthesized signal, from the detectors 231a to 231d, are stored in the storage unit 290 via the entire control unit 250.

The entire control unit 250 implements the control for the entire optical wafer surface inspection apparatus, for example, implements a process corresponding to an operation signal by receiving the operation signal from the input operation unit 280 and using a program stored in the storage unit 290. The stage control unit 260 outputs an instruction signal for controlling the rotation drive unit 213 and slide drive unit 214 in the sample inspection table 210 and changes an operation condition for synthesizing the detected signals, digitalized in the signal synthesizing unit 240, from the detectors 231a to 231d.

The entire control unit 250 stores the data of synthesized signal synthesized in the signal synthesizing unit 240 and of the digitalized detected signal, originated for the synthesized signal, from the detectors 231a to 231d in the storage unit 290 and uses a processing program stored in the storage unit 290 to process these pieces of data and display it on the information display unit 270. In addition, FIG. 2 illustrates the signal synthesizing unit. However, the signal synthesizing unit 240 is unnecessary for passing through itself when the entire control unit 250 processes directly the data extracted individually or partly the signals from the detectors 233a to 233d to display on the information display unit 270. In this case, either all or part of the signals from the detectors 233a to 233d are sometimes stored directly in the storage unit 290, and either all or part of the signals from the detectors 233a to 233d are sometimes processed in the entire control unit 250 to store in the storage unit 290.

The input operation unit 280 is used for entering a synthesis condition of the detected signal by a user in signal synthesizing unit 240, as mentioned above, and used for instructing the operation etc. of devices.

The storage unit 290 stores programs/constants necessary for various control/operation processes, measured results (synthesized signal and detected signal), the synthesis conditions set by the input operation unit 280, etc. The data of synthesized signals and detected signals respectively from the detectors 231a to 231d are stored with a measured position (coordinates), acquired from the stage control unit 260, of the scattering light on the wafer.

The communication unit 295 is coupled with the network 140, and the entire control unit 250 implements to transmit and receive data to/from the data server 120 and a design information database 130 via the communication unit 295.

Figure 3:
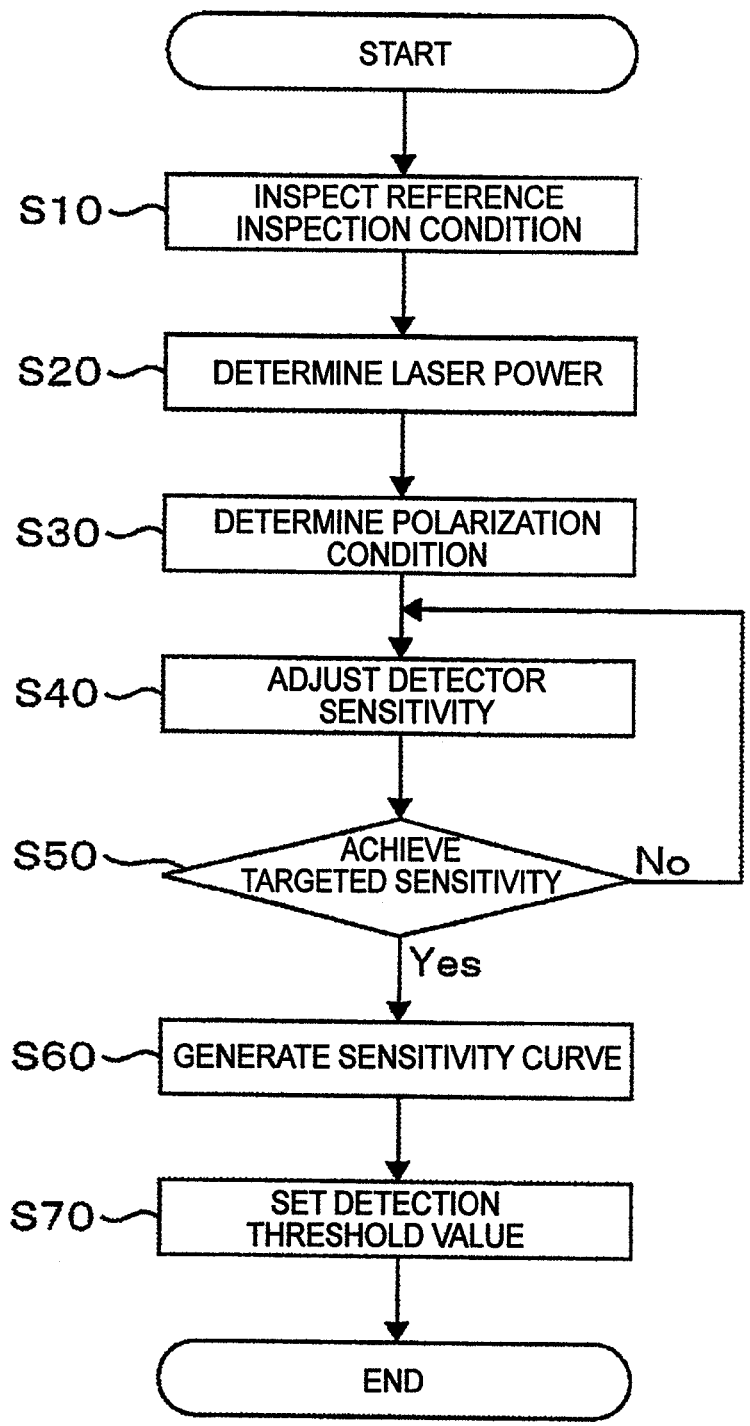
FIG. 3 is a generating procedure of an inspection condition for the optical wafer surface inspection apparatus in the embodiment of the invention.

FIG. 3 shows an example of a procedure for generating the inspection condition of the optical wafer surface inspection apparatus. A wafer, on which the standard particles of plural sizes are applied to plural locations as shaped a spot, is prepared for every layer type and layer thickness to generate the inspection condition by the following procedure. First, the wafer prepared for every above-mentioned layer type and layer thickness is inspected for a reference inspection condition by the reference inspection condition previously registered in the wafer surface inspection apparatus 100, at a step S10. The reference inspection condition is a parameter set requirement so as to easily acquire the scattering intensity from the standard particles applied on the wafer and various information from the wafer, such as a noise etc. acquired from the wafer surface. A laser power is determined from an inspected result acquired at the step S10 as inspected the reference inspection condition, at a step S20, to acquire an optimal laser power on the inspected wafer. Further, at a step S30 as determined a polarization condition, the polarization condition of illumination light to be irradiated on the wafer is switched over to inspect the wafer by using a polarization switching-over mechanism built in the illumination light source 220 and select the most preferable polarization condition of S/N ratio (ratio for signal and noise) from among the inspections. An irradiation condition is determined by the above-mentioned procedure, therefore, a condition for a detecting system is determined at a step S40 as adjusted a detector sensitivity, next. The wafer is inspected by using the irradiation condition determined at the step S20 as determined the laser power and the step S30 as determined the polarization condition to adjust the parameters of the detectors 231a to 231d. Here, the process determines whether a targeted sensitivity is acquired at a step S50. If the targeted sensitivity is not acquired, the process adjusts the detector sensitivity at the step S40. If it is acquired, the process generates a sensitivity curve at a step S60. In this way, the condition for a light irradiation and reception system is determined, and the scattering intensity, acquired from the standard particle sizes applied to the wafer, is decided, therefore, a relation between the scattering intensity of the standard particle for each of the sizes and the standard particle size is determined. The relation between the scattering intensity of the standard particle for each of the sizes and the size of the standard particle is referred to as the sensitivity curve to be used for transforming the scattering intensity acquired from the inspection apparatus to the size. Finally, the inspection condition is completed by implementing a step S70 as set a detector threshold value for separating the scattering intensity from the standard particles applied on the wafer and the noise generated from the wafer surface etc.

Figure 4:
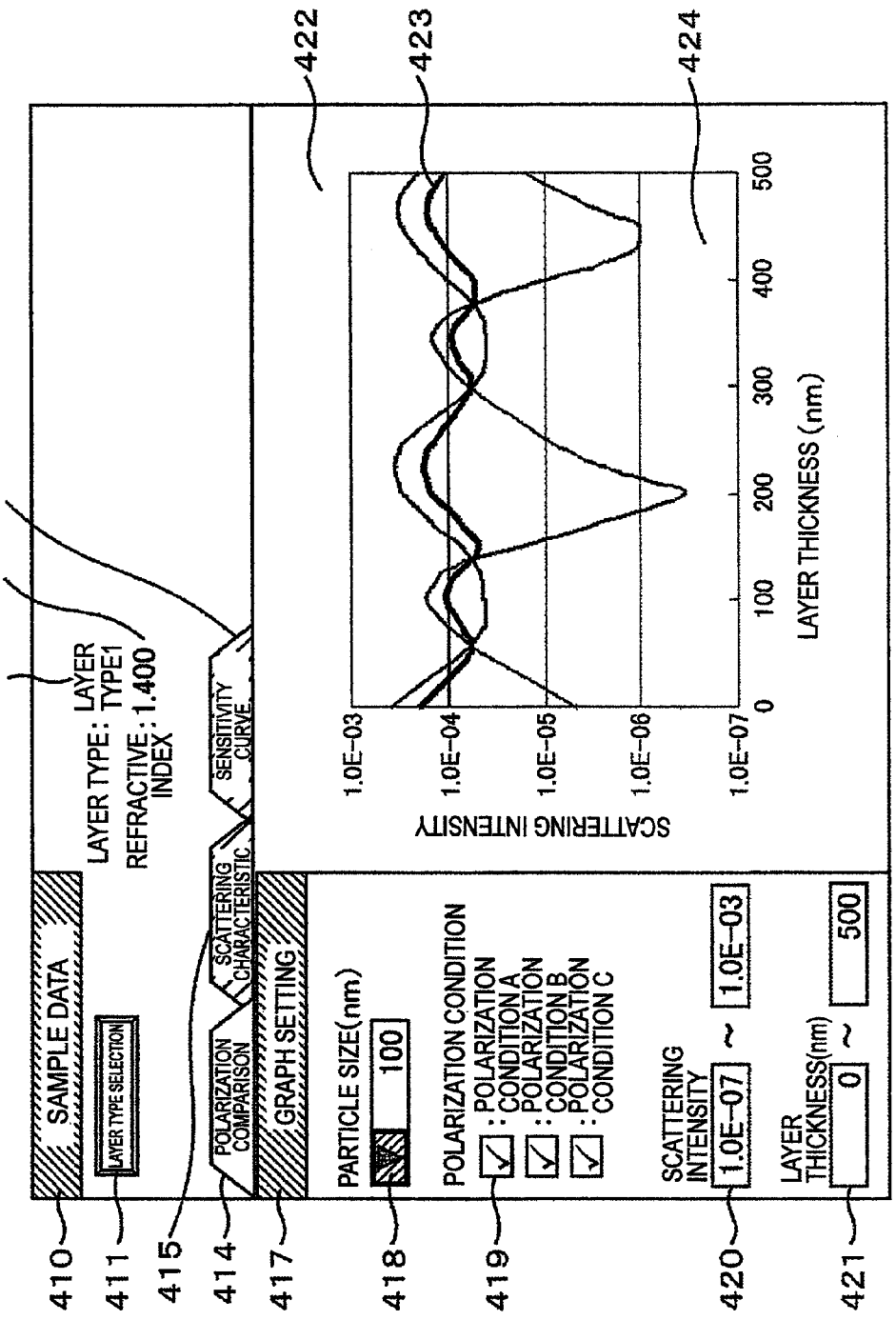
FIG. 4 is a scattering intensity characteristic data comparison screen for every polarization condition in the embodiment of the invention.
Figure 5:
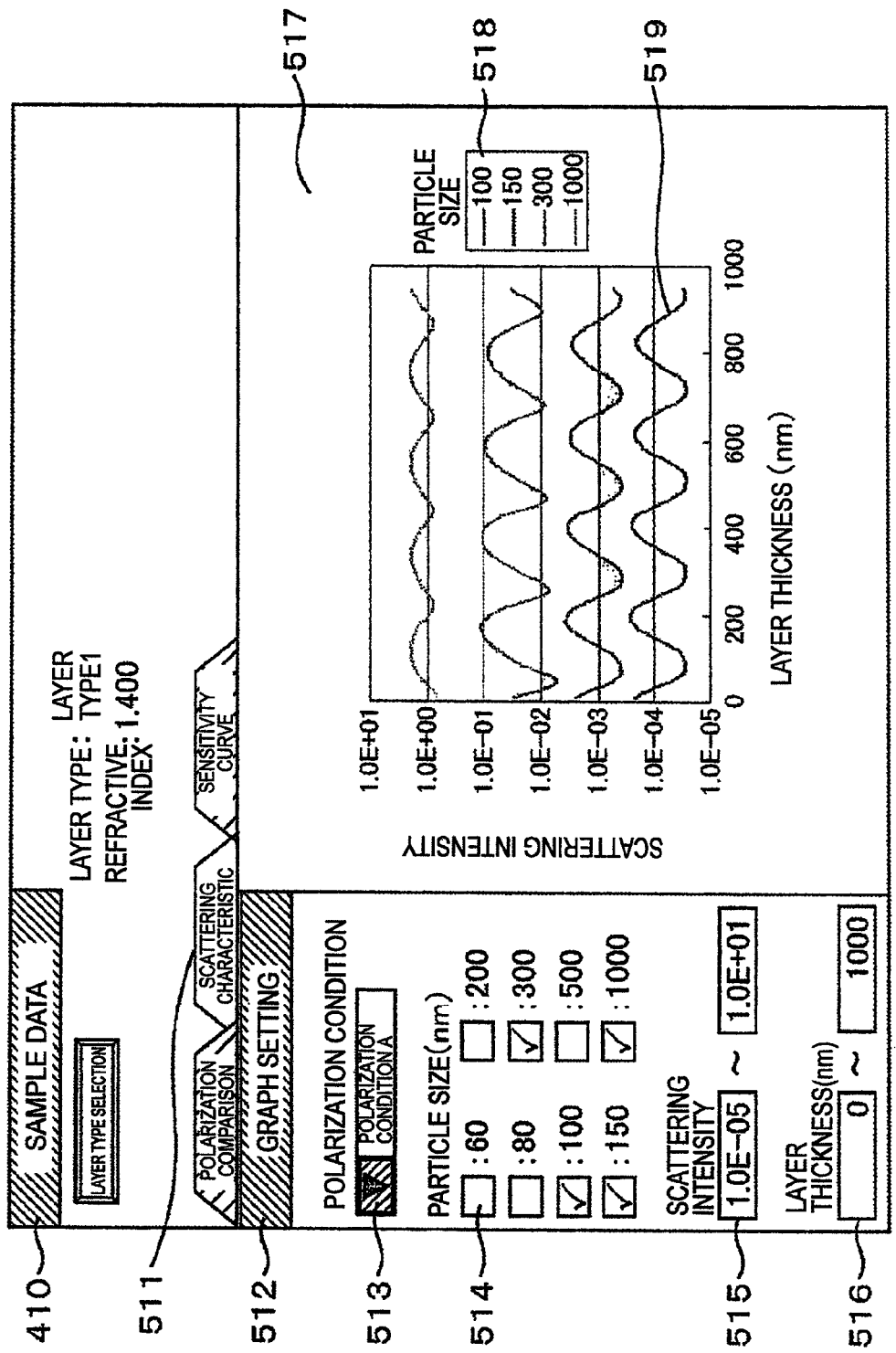
FIG. 5 is a scattering intensity characteristic data confirmation screen for every particle size in the embodiment of the invention.
Figure 6:
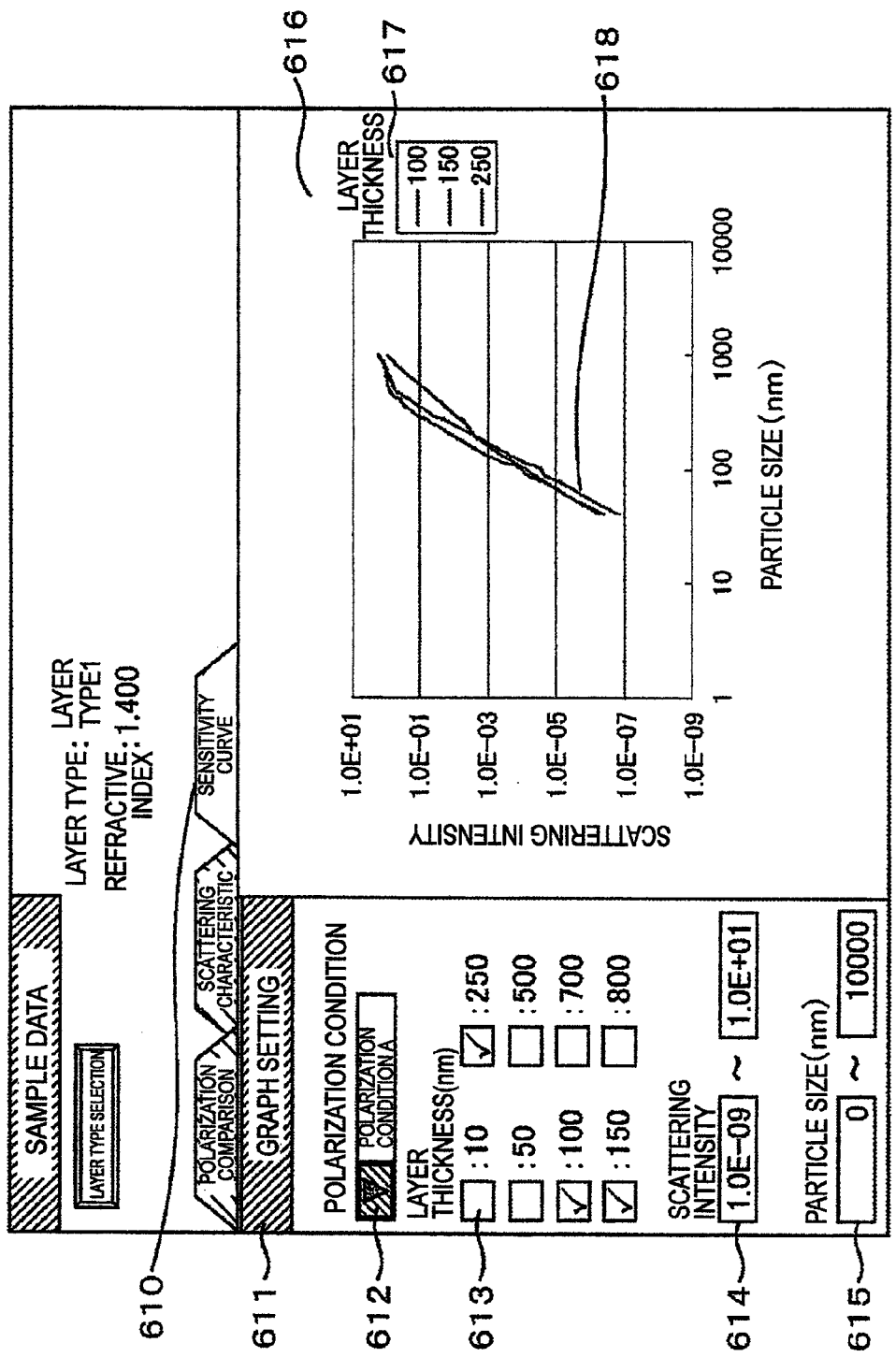
FIG. 6 is a sensitivity curve confirmation screen for every layer thickness in the embodiment of the invention.

FIG. 4 to FIG. 6 show screens for displaying information necessary for when the layer type data for examining a sharing of the inspection conditions is read out from the scattering intensity characteristic database 110 regarding the layer thickness for every layer type calculated by the simulator 111 held in the data server 103 to then inquire and select the polarization condition and the detected particle size appropriate to the sharing of inspection conditions. There are a polarization comparison item for comparing the scattering intensity characteristic data for every polarization condition, a scattering characteristic item for confirming the scattering intensity characteristic data for every particle size and a sensitivity curve item indicating an interrelation between the particle size for every layer thickness and the scattering intensity, and a display screen for the items can be switched over to the display by clicking a polarization comparison tab 414, a scattering characteristic tab 415 and a sensitivity curve tab 416.

FIG. 4 shows the screen of polarization comparison item. This is made up of a sample data display column 410 for displaying various information of the layer formed on the substrate, a scattering intensity characteristic data display column 422 displaying as a graph such that the scattering characteristic data, in the scattering intensity characteristic database 110 regarding the layer thickness for every layer type calculated by the simulator 111 held in the data server 103, can be compared and confirmed easily, and a graph setting display column 417 for setting display data, such as a display range of the layer thickness and scattering intensity, particle size, polarization condition, etc. in a graph 422 of the scattering characteristic data in the scattering intensity characteristic database 110. A button 411 is clicked to display a layer type list held the scattering intensity characteristic data from the data server 103. A layer type for inquiring and selecting the polarization condition and detected particle size suitable for sharing the inspection condition from among the layer type list, is selected to display the selected layer type on a layer type display column 412 and display a refractive index of the selected layer type on a refractive index display column 413. In addition, a method of retrieving the scattering intensity characteristic data from the data server 103 can be considered to use a retrieval etc. using a layer type name and the refractive index.

Scattering characteristic data 423 of the polarization conditions is displayed so as to overlap on the scattering characteristic data display column 422, in relation to the layer type of selecting the scattering characteristic regarding the layer thickness for every layer type held in the data server 103 by the button 411. In this way, the comparison of the scattering characteristic data for each of the polarization conditions is made easy for the layer type selected by the button 411, and the inquiry and selection of the polarization condition suitable for sharing the inspection condition are also made easily. The polarization condition introductory 423 illustrates that it indicates which of the polarization conditions corresponds to the displayed layer type. The scattering characteristic data 423 held in the data server 103 holds not only the scattering characteristic for every layer type, but also the scattering characteristic data for every particle size. The graph setting column 417 has a pull-down menu 418 for selecting the particle size from among the scattering characteristic data, that is, from among the particle sizes held in the scattering characteristic database regarding the layer thickness for every layer type held in the data server 103. There is a polarization condition selecting check box 419 for selecting the scattering characteristic data of necessary polarization condition from the scattering characteristic data regarding the particle size for every selected polarization condition. The scattering characteristic data of polarization condition, selected by the polarization condition selecting check box 419, is displayed on the scattering characteristic data display column 422. Further, a scattering intensity display range for the scattering characteristic data display column 422 can be specified by a scattering intensity range specifying column 420 so that the scattering characteristic data for every displayed polarization condition is displayed in detail to compare with each other. A layer thickness range specifying column 421 can specify the display range of layer thickness in the scattering characteristic data display column 422. The display range of the scattering intensity and layer thickness are determined automatically in response to the displayed scattering characteristic data 423 when the scattering intensity range specifying column 420 and layer thickness range specifying column 421 are not specified, and values in the display range at this time are displayed respectively on the scattering intensity range specifying column 420 and layer thickness range specifying column 421.

As mentioned above, the scattering characteristic for every polarization condition regarding the layer thickness for every layer type in the data server 103 is compared with each other on the polarization comparison item screen in FIG. 4, so that a variation of the scattering intensity regarding the layer thickness can be made little and the inquiry and selection of the polarization condition suitable for sharing the inspection condition can be made easily.

Next, FIG. 5 shows a screen of the scattering characteristic item for confirming the scattering intensity characteristic data for every particle size. The sample data display column 410 is common with the polarization comparison item in FIG. 4, that is, the selected layer type and refractive index are displayed. A scattering characteristic tab 511 is clicked to display the scattering intensity characteristic regarding the layer thickness for every particle size on a scattering intensity characteristic display column 517, and setting contents corresponding to the scattering intensity characteristic display column 517 are displayed automatically on a graph setting column 512.

A polarization condition pull-down menu 513 lies in the graph setting column 512, for selecting the polarization condition of the scattering intensity characteristic to be displayed on the scattering intensity characteristic display column 517 to be able to display the scattering characteristic data of the polarization condition selected by the polarization condition pull-down menu on the scattering intensity characteristic display column 517. The particle size of the scattering intensity characteristic held in the data server 103 is displayed on a particle size selecting check box, and a scattering intensity characteristic 519 of the particle size entered as a check in the check box is displayed on the scattering intensity characteristic display column 517. A particle size introductory 518 displays values as checked in a particle size selecting check box 514. Further, the scattering intensity display range specifying column and layer thickness display range specifying column have the same function as that in the polarization condition comparison tab.

FIG. 6 shows a screen of the sensitivity curve item indicating the interrelation between the particle size for every layer thickness and the scattering intensity. A sensitivity curve item screen is configured by a polarization comparison item, a sample data display column likewise the scattering characteristic item and a sensitivity curve display column 616 indicating an interrelation between the particle size for every layer thickness in a graph setting column 611 and the scattering intensity. A sensitivity curve tab 610 is clicked to display automatically contents corresponding to the sensitivity curve item of the graph setting column 611 and sensitivity curve display column 616.

A polarization condition pull-down menu 612 lies in the graph setting column 611, for selecting the polarization condition of the scattering intensity characteristic to be displayed on the scattering intensity characteristic display column 616, and the scattering characteristic data regarding the layer thickness different in the polarization condition is anytime switched over to be able to display it as required. The layer thickness in the scattering intensity characteristic held in the data server 103 is displayed on a layer thickness selecting check box, and a scattering intensity characteristic 618 of the layer thickness entered as a check in the check box is displayed on the scattering intensity characteristic display column 616. A layer thickness introductory 617 is displayed with values checked in a layer thickness selecting check box 613. Further, the scattering intensity display range specifying column and layer thickness display range specifying column have the same function as that in the polarization condition comparison tab and the scattering characteristic tab.

As mentioned above, the scattering intensity characteristic regarding the layer thickness for every layer type held in the data server 103 is analyzed by using the polarization comparison item in FIG. 4, the scattering characteristic item in FIG. 5 and the sensitivity curve item in FIG. 6, so that the optimal polarization condition, detected particle size, etc. can be selected to share the inspection condition. The optimal polarization condition, detected particle size, etc. are selected, therefore, an error generated by sharing the inspection condition is inhibited in minimum to be able to implement the inspection stably.

Figure 7:
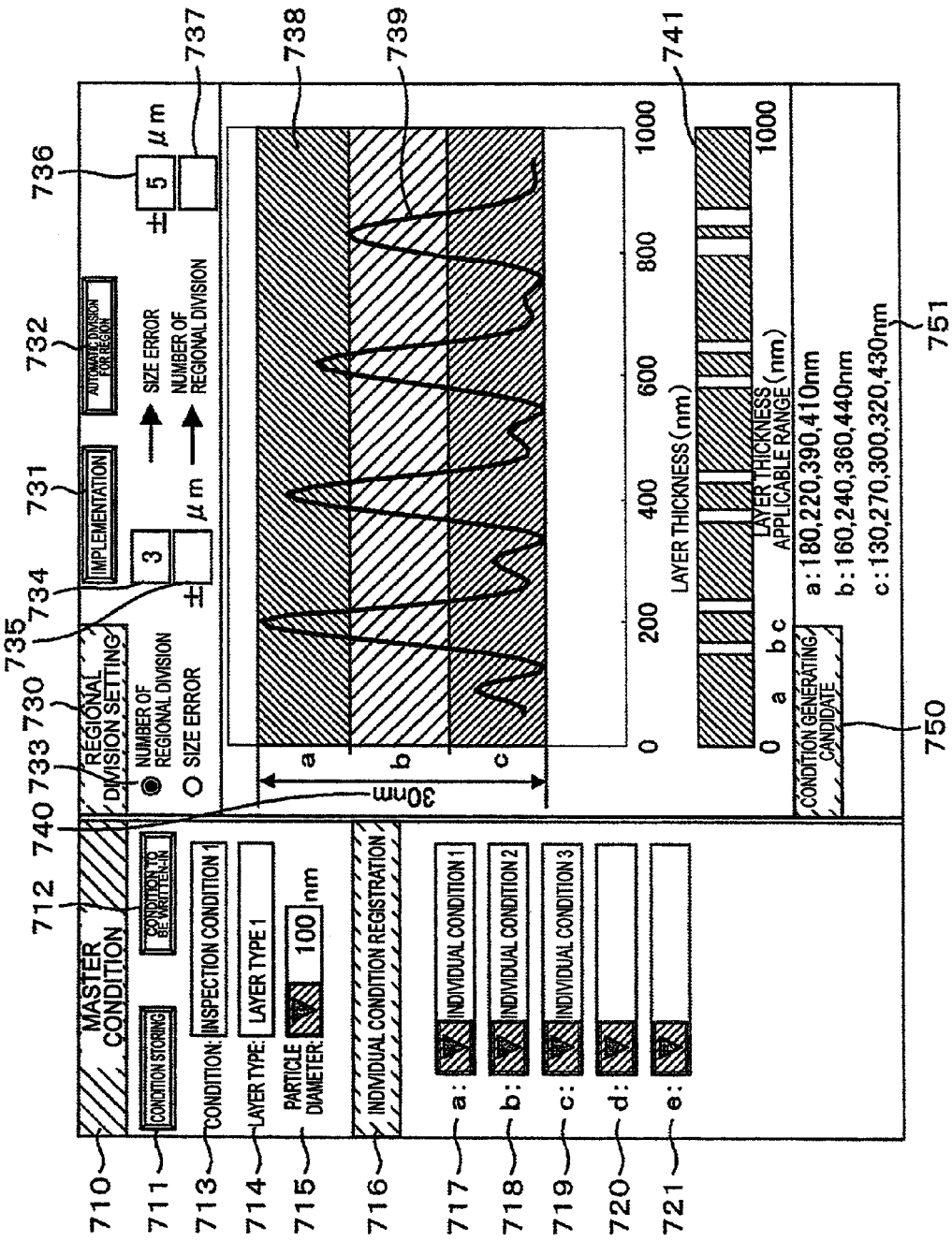
FIG. 7 is an inspection condition sharing setting screen in the embodiment of the invention.

FIG. 7 shows a maser condition setting screen for setting parameters for dividing the scattering intensity into plural regions as classified by the intensity and sharing the inspection condition.

A storing and write-in of a master condition, a condition registration of the divided regions, etc. are implemented on a master condition column 710. The master condition includes various information necessary for sharing the requirement, such as a divisional setting of the scattering intensity, registration information of the plural conditions generated for every the scattering intensity region. A button 711 is clicked to store the master condition, and a button 712 is clicked to be able to write-in the already generated master condition. An arbitrary master condition name is entered into a text box 713, which is used for selecting the master condition etc. on an inspection screen etc. Further, a pull-down menu 714 is used for selecting the layer type for use in a setting from the scattering intensity characteristic calculated by the simulator 111. Furthermore, a particle diameter of the already calculated scattering characteristic is selected by a pull-down menu 715 from among the layer types selected by the pull-down menu 714. In consequence, a size error range 740 of the scattering intensity characteristic transformed a scattering intensity characteristic 739 regarding the selected layer type and particle diameter and the variation width of scattering intensity to a size by using the sensitivity curve, is displayed automatically.

In an individual condition registering column 716, the plural inspection conditions selected from pull-down menus 717 to 721 are registered in the master condition. Wafer information is entered by the inspection screen to implement the inspection, select automatically the inspection condition corresponding to the scattering intensity of the inspection targeted wafer and implement the inspection. In a scattering intensity regional division setting column 730, a setting regarding the division of the scattering intensity region is implemented for the scattering intensity characteristic 739. The setting method includes plural ones: a method of specifying the number of dividing the scattering intensity region, a method of specifying a size error caused by dividing the scattering intensity region to share the inspection condition, etc. The method of dividing the scattering intensity region is selected by a radio button 733, and the number of dividing the scattering intensity is entered into a text box 734 to display the size error on a text box 736, generated by when dividing the scattering intensity region by the specified number of division. When the size error is selected, the size error is entered into a text box 735 to display the number of division of when the scattering intensity is divided, on a text box 737 such that the error specified by the text box 735 is entered into the text box 737, and such result is displayed on a scattering intensity divided result 738. The number of division for region is selected when specifying the number of necessary inspection condition since the number of scattering intensity region is equal to the number of necessary inspection condition. The size error is specified to divide the scattering intensity region when specifying the size error in dividing the scattering intensity region. As mentioned above, as a result of dividing the scattering intensity region, an applicable layer thickness range for every scattering intensity dividing region is distinguished by different colors to be displayed on a layer thickness applicable range 741.

As the result of dividing the scattering intensity region, the layer thickness necessary for generating the inspection condition for every divided region is displayed automatically on a condition generation optional list 751. One layer thickness is selected from among the layer thicknesses displayed for every region to prepare a wafer and generate a requirement.

Figure 8:
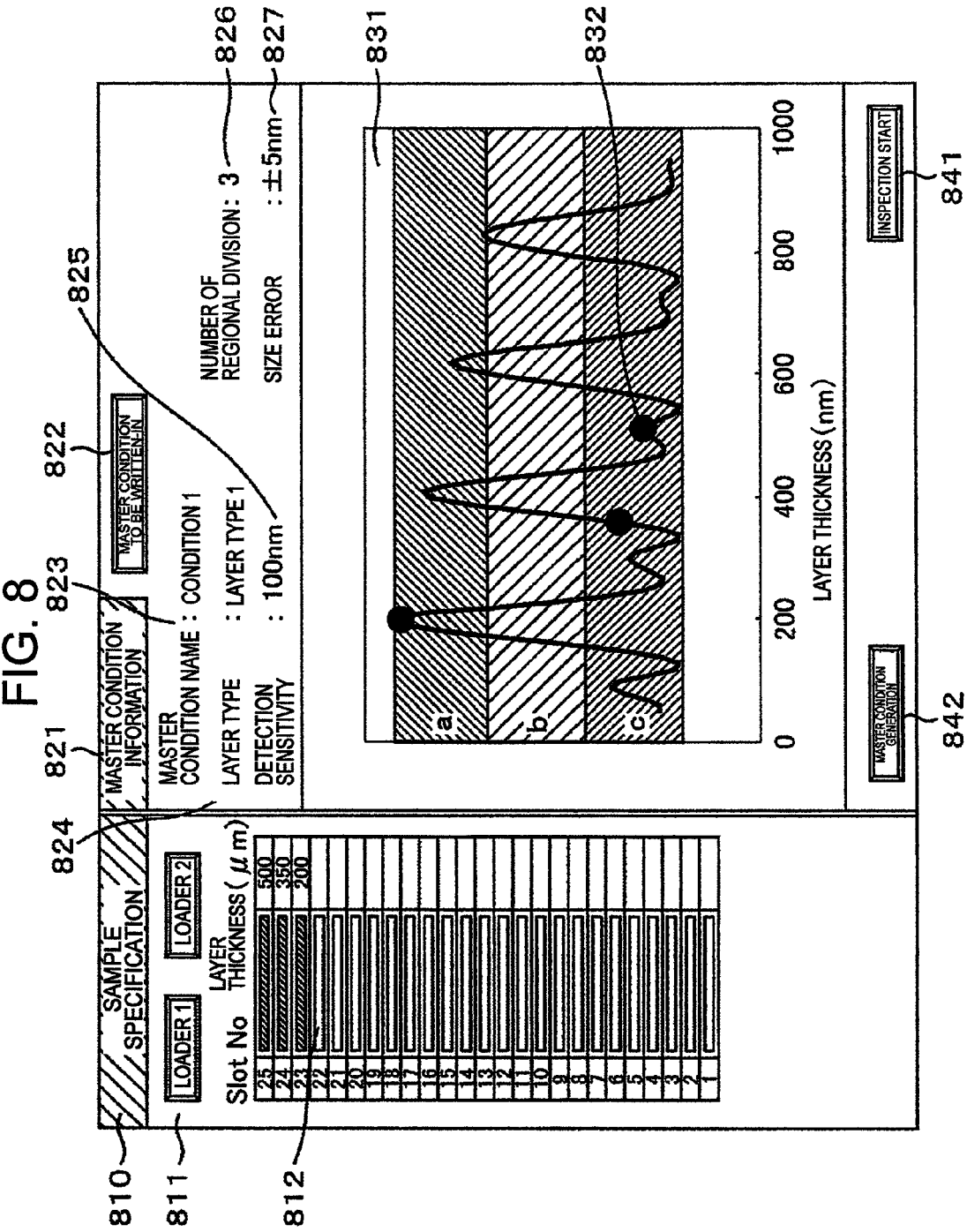
FIG. 8 is an inspection implementation screen in the embodiment of the invention.

FIG. 8 is an inspection setting screen for specifying the wafer and master condition when the wafer is inspected by the inspection apparatus with use of the master condition shared the inspection condition. A sample specification column 810 includes a loader selection button 811 for selecting a loader loading the inspection targeted wafer from among plural loaders in the inspection apparatus and a wafer specification column 812 for entering a selection of wafer shelf number and the layer thickness of the wafer. Master condition information 821 is a column for displaying information of a write-in the inspection condition and of written-in inspection condition. A button 822 is clicked to select the master condition from a master condition list and display a master condition name on a condition name display column 823, the layer type targeted by a written-in master condition on a layer type display column 824, the detected sensitivity of the written-in master condition on a detected sensitivity display column 825, the number of scattering intensity division of the written-in master condition on a number of region division display column 826, and the size error caused by the scattering intensity division of the written-in master condition on a size error display column 827. A scattering intensity characteristic display column 831 is displayed when selecting the master condition by the button 822, and an inspection wafer display maker 832 is displayed automatically when entering the layer thickness of wafer into the wafer specification column 812. A button 842 is used for moving to the master condition setting screen, and a button 841 is used for implementing the inspection by the master condition.

As mentioned above, the inspection condition for the inspection apparatus is made optimal and shared for every scattering intensity region. In this way, the operation of generating the inspection condition for the inspection apparatus can be reduced drastically, even though it has taken a great period of time and cost for preparing the wafer for every layer type and layer thickness and applying the standard particles to these wafers. The layer type already shared the inspection condition is not required to prepare a new wafer and generate the inspection condition even when changing the layer thickness caused by a process change. The inspection can therefore be made rapidly and a yield can be tried to improve by an early discovery for a process abnormality. The operation time and cost for generating the inspection condition can be reduced drastically by calculating the relation between the layer thickness and the scattering intensity in the inspection apparatus, dividing the scattering intensity into plural regions as classified by the intensity, generating the optimal inspection condition for every divided region, and sharing the inspection condition for every divided scattering intensity region.

The operation time and cost for generating the inspection condition can be reduced drastically by calculating the relation between the layer thickness and the scattering intensity in the inspection apparatus, dividing the scattering intensity into plural regions as classified by the intensity, generating the inspection condition for every the divided region, and sharing the inspection condition for every divided scattering intensity region.

A machine start-up time can be shorten drastically after delivery, by reducing the generation time for the inspection condition drastically. The generation for a new inspection condition is not required, but required previously, when the inspection targeted wafer has the same layer type but the layer thickness is varied, so that the inspection can be implemented rapidly. In consequence, it is possible to early discover the process abnormality, therefore, the yield can be tried to improve early.

The inspection condition of the inspection apparatus is divided into the scattering intensity regions, and the inspection condition made optimal in the respective regions is shared to be able to reduce the operation of generating the inspection condition for the inspection apparatus, even though it has taken a great period of time and cost for preparing the wafer for every layer type and layer thickness and applying the standard particles to these wafers. The layer type already shared the inspection condition is not required to prepare a new wafer and generate the inspection condition even when changing the layer thickness, but the same layer type, caused by the process change. The inspection can therefore be made rapidly and the yield can be tried to improve by the early discovery for the process abnormality.

By using an operation device and a memory in another server on an inter network, there is an advantage that the invention can be implemented for the inspection apparatuses located on plural different districts beyond over a closed network, with the case where a storage device, a memory, etc. are shared.

Figure 9:
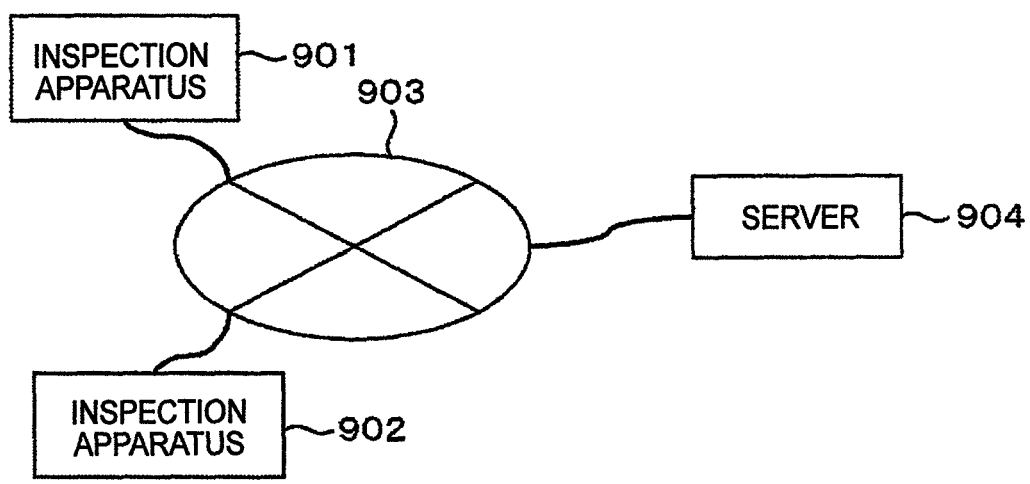
FIG. 9 is a network connection example in the embodiment of the invention.

An example of this procedure will be described with reference to FIG. 9.

A reference numeral 901 denotes the inspection apparatus using the invention, 902 is the inspection apparatus using the invention or inspection apparatus for inspecting a substrate after forming a pattern, 903 is a network such as Internet, and 904 is a server.

In the above-mentioned embodiment, an error sometimes occurs in the result inspected by the optical wafer surface inspection apparatus 100 since the scattering intensity having the variation width is divided into the plural regions as classified by the intensity to inspect by using the same shared condition. FIGS. 10 to 18 show a procedure for reducing that error and its embodiment.

Figure 10:
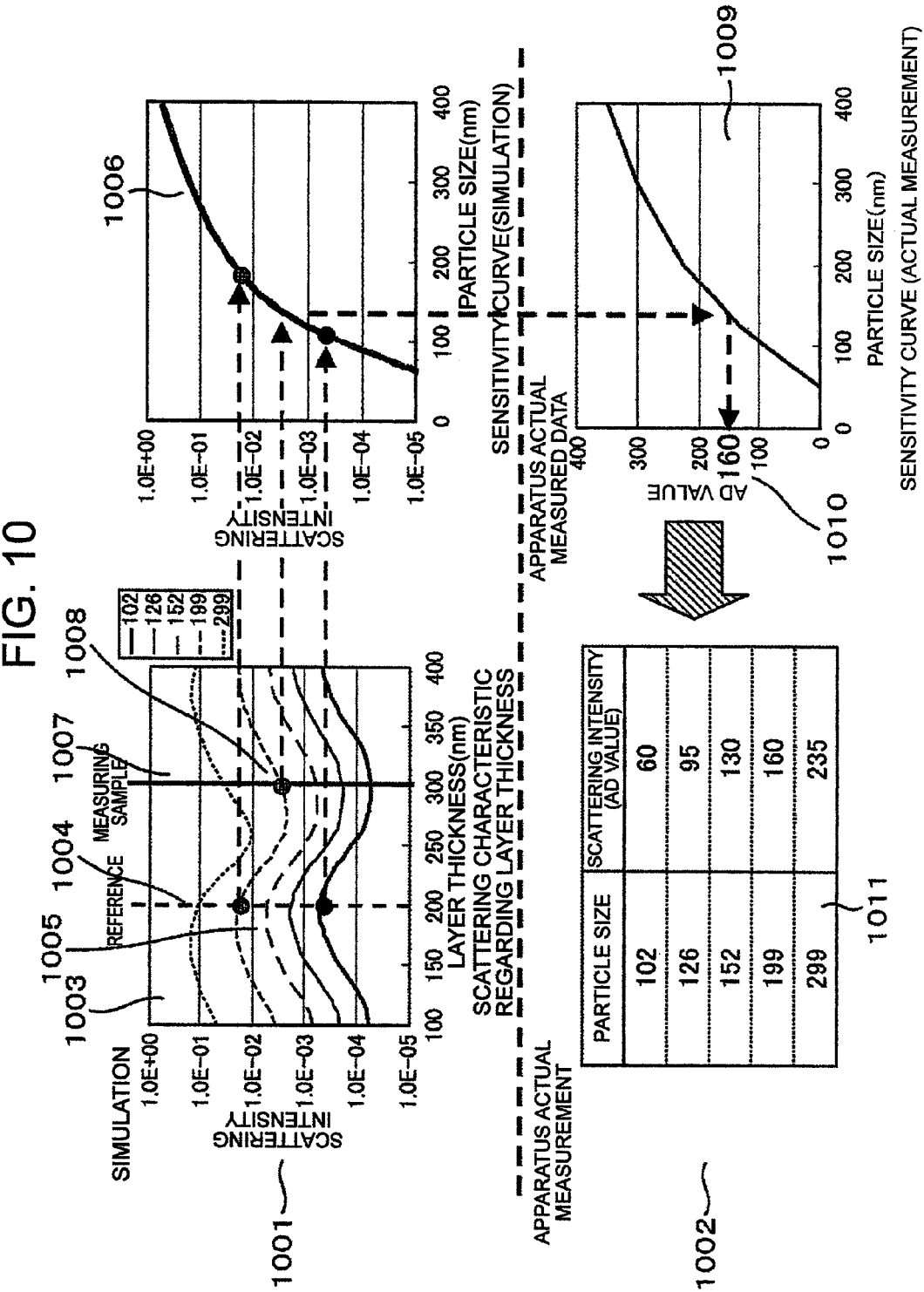
FIG. 10 is an outline of a measurement error reducing procedure in the embodiment of the invention.

FIG. 10 shows an outline of the procedure for reducing the error. A simulation data 1001 is generated from the result calculated by the simulator 111, and an actual measured data 1002 is generated from the result of measuring a standard sample by the apparatus.

A reference layer thickness 1004 is specified from a scattering intensity characteristic 1003 regarding the layer thickness for every layer type calculated by the simulator 111. A scattering intensity 1005 for the particle sizes of the specified reference thickness 1004 is calculated from the scattering intensity characteristic 1003 regarding the layer thickness, and a sensitivity curve (simulation) 1006 is generated from a relation between the particle size and scattering intensity in the reference layer thickness 1004. Next, a scattering intensity 1008 of the particle sizes corresponding to a layer thickness 1007 of the measuring sample is calculated from the scattering intensity characteristic 1003 regarding the layer thickness, and the calculated scattering intensity 1008 of the particles size is transformed to the size by using the sensitivity curve (simulation) 1006. The transformed size is further transformed to an AD value 1010 by using a sensitivity curve (actual measurement) 1009 actually measured and generated by the optical wafer surface inspection apparatus 100. Likewise, the AD value 1010 is also calculated for the other particles of measuring sample to generate a correspondence table 1011 for the particle size and AD value, therefore, the sensitivity curve, acquired from the relation between the particle size and scattering intensity necessary for generating the inspection condition, is acquired. This procedure is not readily affected by a machine difference for every inspection apparatus since the sensitivity curve (actual measurement) 1009, acquired from the relation between the actual measured value and particle size generated for every inspection apparatus, is used.

Figure 11:
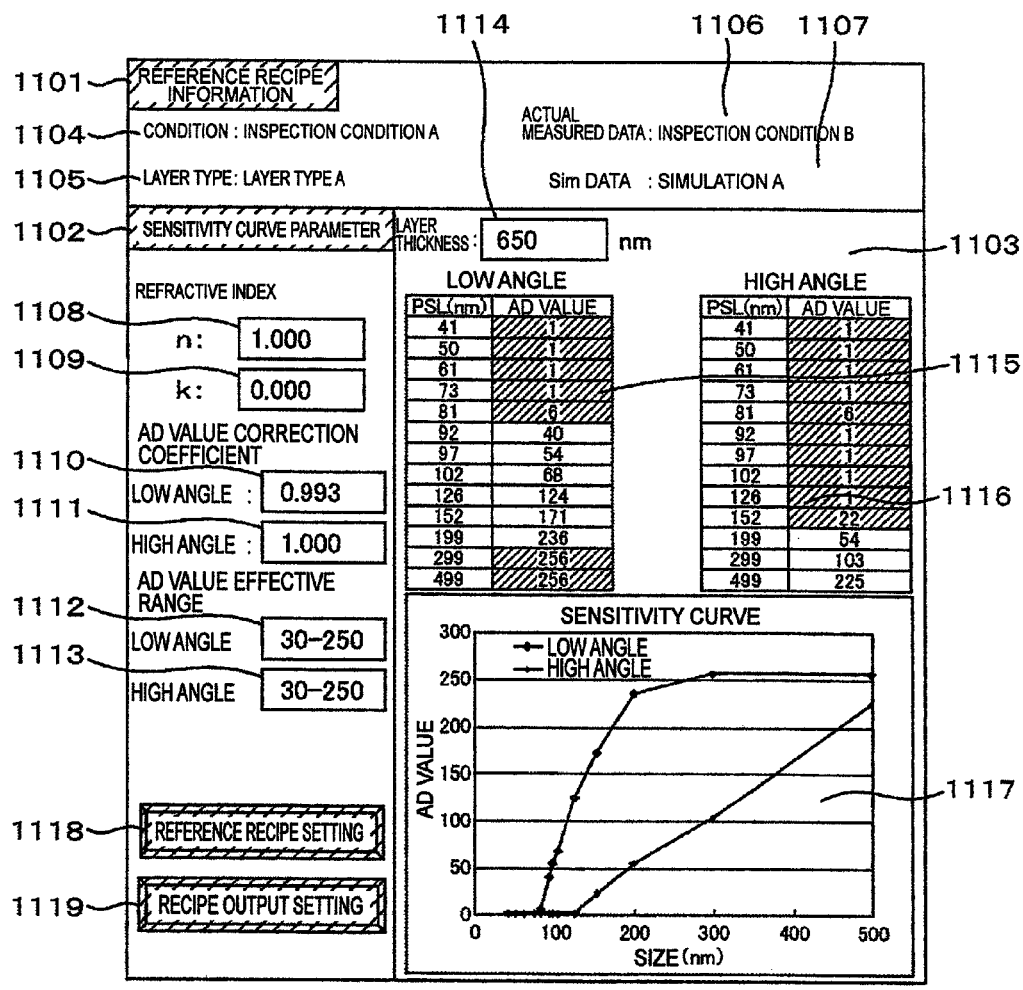
FIG. 11 is a sensitivity curve calculated result display screen in the embodiment of the invention.

Next, an embodiment for the above-mentioned procedure is described below. FIG. 11 is a calculated result screen of the sensitivity curve necessary for when inspecting by the optical wafer surface inspection apparatus 100, which calculated, by using the scattering intensity characteristic 1003 regarding the layer thickness for every layer type calculated by the simulator 111. FIG. 11 shows a sensitivity curve calculated result display screen configured by a referenced recipe information column 1101, a sensitivity curve calculation parameter column 1102 and a sensitivity calculated result display column 1103. A reference recipe setting screens shown in FIG. 12 and FIG. 13 can be displayed by a reference recipe setting button 1118, and a recipe output setting screen shown in FIG. 14 can be displayed by a recipe output button 1119.

Figure 12:
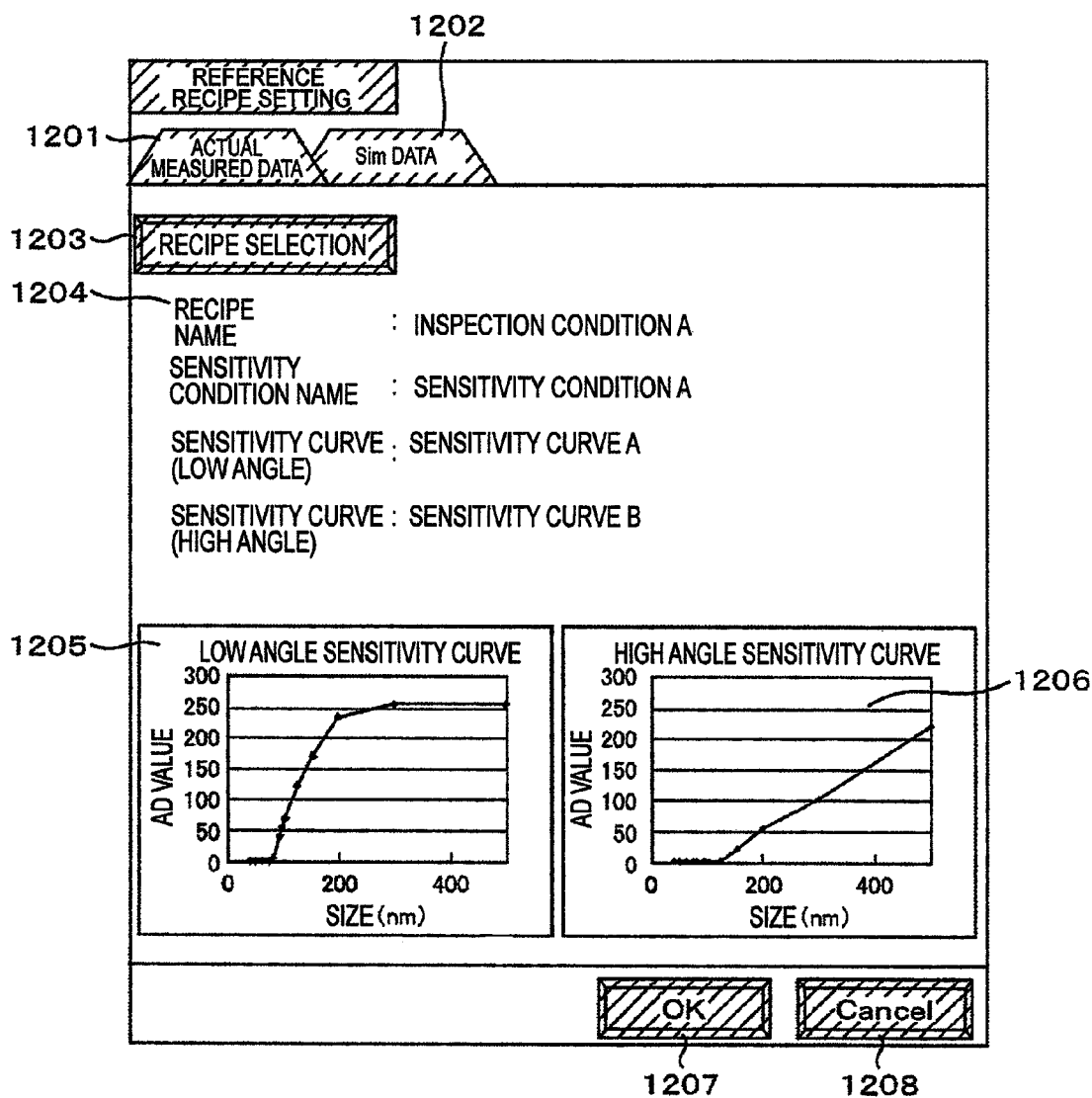
FIG. 12 is an actual measured data screen of reference recipe setting screen in the embodiment of the invention.

In the reference recipe information column 1101, a condition name of reference recipe set by the reference recipe setting shown in FIG. 12 and FIG. 13 is displayed on a condition name display column 1104. A layer type name is displayed on a layer type name display column 1105. A sensitivity curve (actually measured) name is displayed on an actual measured data name display column 1106. A sensitivity curve (simulation) name generated from the scattering intensity characteristic data regarding the layer thickness for every layer type is displayed on a Sim data display column 1107.

The sensitivity curve calculation parameter column 1102 has a refractive index (n) entering column 1108 and a refractive index (k) entering column 1109 for entering the actual measured value of refractive index for the targeted layer type. An actual measured refractive index is entered to calculate a difference from the refractive index used in when calculating the scattering intensity characteristic 1003 by the simulator regarding the layer thickness. The value of scattering intensity characteristic 1003 regarding the layer thickness in response to the difference is corrected to be able to improve a simulation accuracy of the scattering intensity characteristic 1003 regarding the layer thickness for every layer type. An AD value correction coefficient column has a low angle AD value correction coefficient entering column 1110 and a high angle AD value correction coefficient entering column 1111. A correction value 1703 acquired from a compared result of an after-mentioned actual measured value and a simulated value is entered to correct a low angle AD value calculated result 1115 and a high angle AD value calculated result 1116, so that the error can be decreased. An AD value effective range also has a low angle AD value effective range 1112 and a high angle AD value effective range 1113, which sets an effective range of AD value reflected to the recipe regarding the low angle AD value calculated result 1115 and high angle AD value calculated result 1116.

The value other than the set AD value effective range is indicated by changing a color of cells such that it is an inappropriate value for generating the inspection condition of the optical wafer surface inspection apparatus 100.

The sensitivity curve calculated result display column 1103 has a layer thickness entering column 1114, and the layer thickness of the measuring sample 1008 is entered to display a low angle AD calculated result on the low angle AD value calculated result display column 1115 and a high angle AD value calculated result on the high angle AD value calculated result display column 1116.

A sensitivity curve graph 1117 shows a curve display of the low angle AD value calculated result 1115 and high angle AD value calculated result 1116. The reference recipe setting button 1118 is clicked to display a reference recipe setting screen shown in FIG. 12 and the recipe output button 1119 is clicked to display a recipe output setting screen shown in FIG. 14 to be able to set a reference recipe setting and a recipe output setting, respectively.

FIG. 12 shows the reference recipe setting screen. The reference recipe setting screen has an actual measured data tab 1201 and a Sim data tab 1202, and the tabs are clicked to switch over the screen and be able to set to it, respectively. A recipe selection button 1203 on the actual measured data tab 1201 is clicked to inspect the standard sample of reference layer thickness 1004 by the optical wafer surface inspection apparatus 100, and the generated reference recipe is selected to display a recipe name, a sensitivity condition name, a low angle sensitivity curve name and a high angle sensitivity curve name of the reference recipe on a reference recipe (actual measurement) information column 1204. The sensitivity curve registered in the reference recipe is displayed on a low angle sensitivity curve graph 1205 and a high angle sensitivity curve graph 1206. An OK button 1207 is clicked to set the recipe, as the reference recipe, selected by the recipe selection button 1203 to be returned to the sensitivity curve calculated result screen of the sensitivity curve calculated result screen in FIG. 11. A cancel button 1208 is clicked not to set the selected recipe, as the reference recipe, but return to the original reference recipe setting and return to the sensitivity curve calculated result screen of the sensitivity curve calculated result screen in FIG. 11.

The reference recipe selection operated by the recipe selection button 1203 will be described in detail below. The recipe selection button 1203 on the actual measured data tab 1201 is clicked to display a recipe selection screen in FIG. 13. The recipe is selected, as a reference, from a recipe list 1301, and an OK button 1303 is clicked to write-in the specified recipe and be able to set in the reference recipe. A cancel button 1304 is clicked not to change the reference recipe setting and return to the reference recipe setting screen in FIG. 12. Further, when a recipe file is stored in plural holders, the recipe file stored in the other holder is written-in to set the reference recipe, etc., a recipe holder selection button 1302 for specifying the stored holder is clicked to specify the holder storing the recipe file. The holder storing the recipe file is specified to display the recipe stored in the holder on the recipe list and be able to select the reference recipe from the list.

Figure 14:
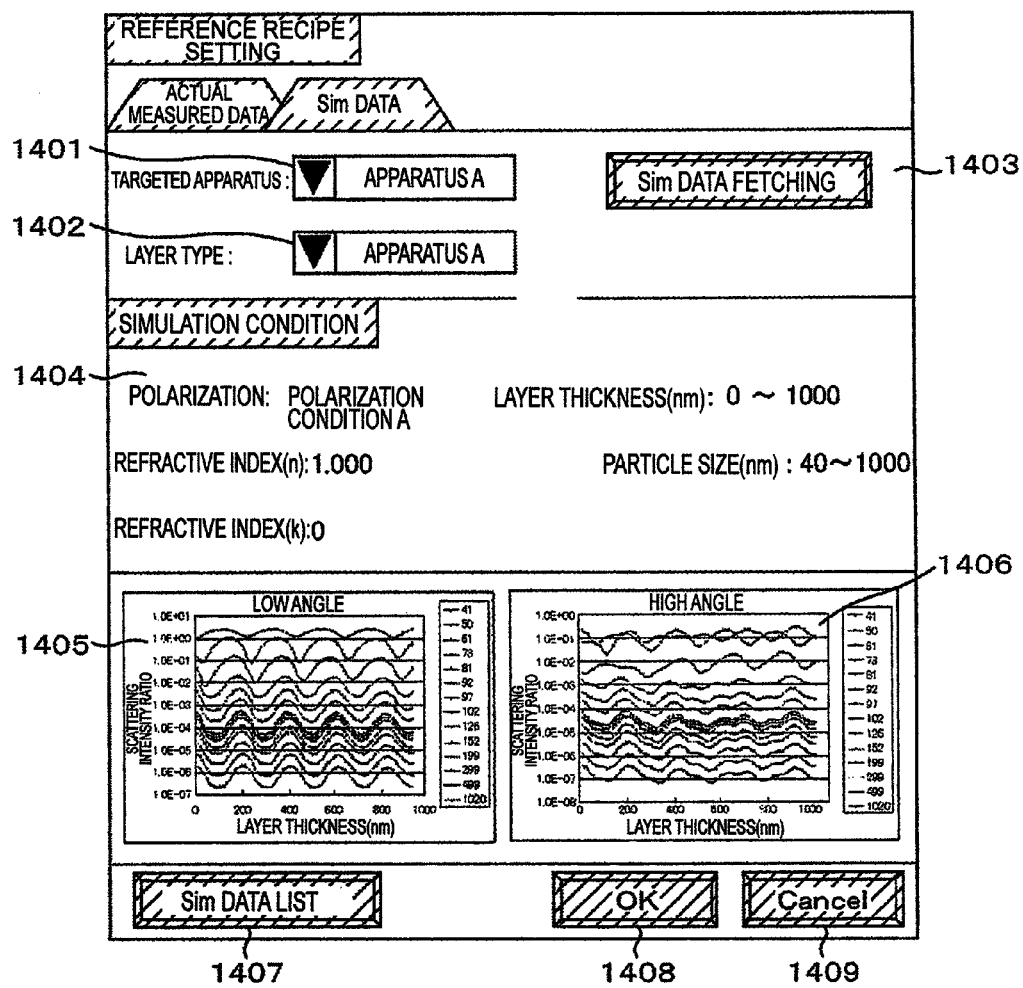
FIG. 14 is a simulation data screen of the reference recipe setting screen in the embodiment of the invention.

The Sim data tab 1202 on the reference recipe setting screen in FIG. 12 is clicked to switch over to a simulation data setting screen in FIG. 14. Since the scattering intensity characteristic 1003 regarding the layer thickness for every layer type calculated by the simulator 111 is different in the data depending on the configuration of inspection apparatus, it is required to prepare the scattering intensity characteristic 1003 regarding the layer thickness for every layer type for each configuration of the inspection apparatuses, therefore, it is required to select the scattering intensity characteristic 1003 regarding the layer thickness for every layer type in correspondence to the configuration of inspection apparatus. The inspection apparatus for use in the inspection is selected from a pull-down menu 1401 to select the targeted layer type from a pull-down menu 1402. A simulation condition of the scattering intensity characteristic 1003 regarding the layer thickness for every layer type selected from the pull-down menus 1401, 1402 is displayed on a simulation condition display column 1404. An item to be displayed on the simulation condition display column 1404 is considered to have an optical condition, a refractive index of targeted layer type, layer thickness, particle size, etc. Graphs of the scattering intensity characteristic 1003 regarding the layer thickness in the inspection apparatus and layer type selected respectively by the pull-down menu 1401 and pull-down menu 1402 are displayed respectively on a low angle scattering intensity characteristic graph 1405 and a high angle scattering intensity characteristic graph 1406. When the scattering intensity characteristic 1003 regarding the layer thickness for every layer type calculated separately by the simulator 111 is newly added, a Sim data fetching button 1403 is clicked to specify the data file of scattering intensity characteristic 1003 regarding the separately generated layer thickness for every layer type. A Sim data list button 1407 is clicked to display a simulation data list screen shown in FIG. 15 and be able to display a list 1502 of the scattering intensity characteristic 1003 regarding the layer thickness for every registered layer type. When the scattering intensity characteristic 1003 regarding the layer thickness for every layer type for the plural apparatuses is registered, the inspection apparatus to be targeted on a pull-down menu 1501 is switched over to display the list 1502 of the scattering intensity characteristic 1003 regarding the layer thickness for every layer type corresponding to the selected inspection apparatus. An OK button 1503 is clicked to return to the reference recipe setting screen in FIG. 14.

A recipe output button 1117 on the sensitivity curve calculated result screen in FIG. 11 is clicked to display a recipe output setting screen shown in FIG. 16. The recipe output setting screen in FIG. 16 is configured by an inspection condition display column 1601, a recipe name entering column 1602, a sensitivity curve setting column 1603 and a CH setting column 1604. The inspection condition display column 1601 displays a laser power of the optical wafer surface inspection apparatus 100 for acquiring AD value regarding the particle sizes set by the sensitivity curve setting column 1603 and various inspection conditions 1605 including detector parameters etc. The recipe name entering column 1602 has a recipe name entering column 1606, a low angle sensitivity curve name entering column 1607 and a high angle sensitivity curve entering column 1608 to be able to specify the name of when outputting the generated recipe, low angle sensitivity curve and high angle sensitivity curve. The recipe name entering column 1602 also displays a low angle sensitivity curve column 1609 and a high angle sensitivity curve column 1610 regarding the particle sizes of the low and high angles for the layer thickness calculated and specified on the sensitivity curve calculated result screen shown in FIG. 13. The AD value to be acquired from the inspection of the optical wafer surface inspection apparatus 100 is entered into either the low angle sensitivity curve column 1609 or high angle sensitivity curve column 1610 to calculate respectively the AD value of the other particle sizes in the low and high angle, as a reference of the entered AD value. Further, an inspection condition update button 1611 to calculate the inspection condition necessary for acquiring the set AD value from the inspection of the optical wafer surface inspection apparatus 100 and display on the inspection condition display column 1605. The CH setting column 1604 has a low angle CH setting column 1612 and a high angle CH setting column 1613 to be able to set CH for displaying the piece of inspection for every size to the low and high angle. As mentioned above, in the calculated inspection condition and sensitivity curve, a recipe output button 1614 is clicked to output the inspection condition, also containing the low angle sensitivity curve 1609 and high angle sensitivity curve 1610, of the optical wafer surface inspection apparatus 100 as the recipe name specified by the recipe name input column 1606. A sensitivity curve output button 1615 is clicked to output respectively as a high angle sensitivity curve name specified by the low angle sensitivity curve name and high angle sensitivity curve name entering column 1608 entered on the low angle sensitivity curve name entering column 1607. The inspection is implemented in the optical wafer surface inspection apparatus 100 by using the output recipe or sensitivity curve to be able to measure with the set sensitivity. A cancel button is clicked to return to the sensitivity curve calculated result screen in FIG. 11.

Figure 17:
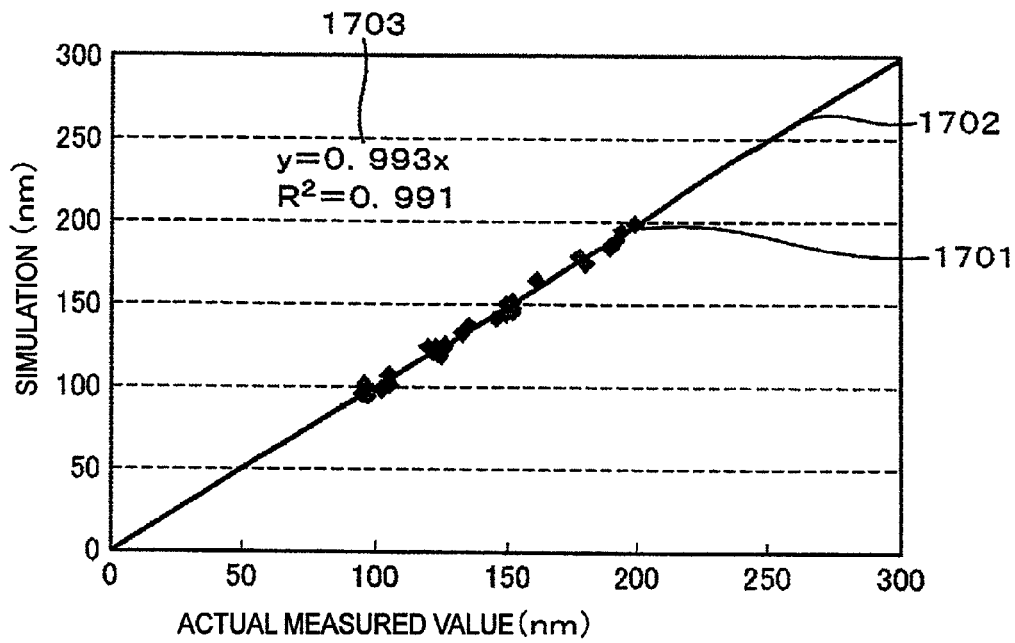
FIG. 17 is a calculated example of AD value-corrected value in the embodiment of the invention.

FIG. 17 shows a calculated example of the AD value correction coefficient in the sensitivity curve calculated result screen in FIG. 11. Wafers respectively having plural layer thicknesses and applied with the standard particles respectively having plural sizes are prepared for every layer type, and the wafers are inspected by the optical wafer surface inspection apparatus 100. An inspection result of when the wafers for every layer type and layer thickness are inspected by the optical wafer surface inspection apparatus 100, is calculated by the simulator 111. An actual measured value by the inspection apparatus is set to X-axis, and a value calculated by the simulator 111 is set to Y-axis. A size of the particles 1701 is plotted to calculate an inclination 1703 of an approximate line-liked straight line 1702 by the least-squares method. This inclination becomes the AD value correction coefficient.

Figure 18:
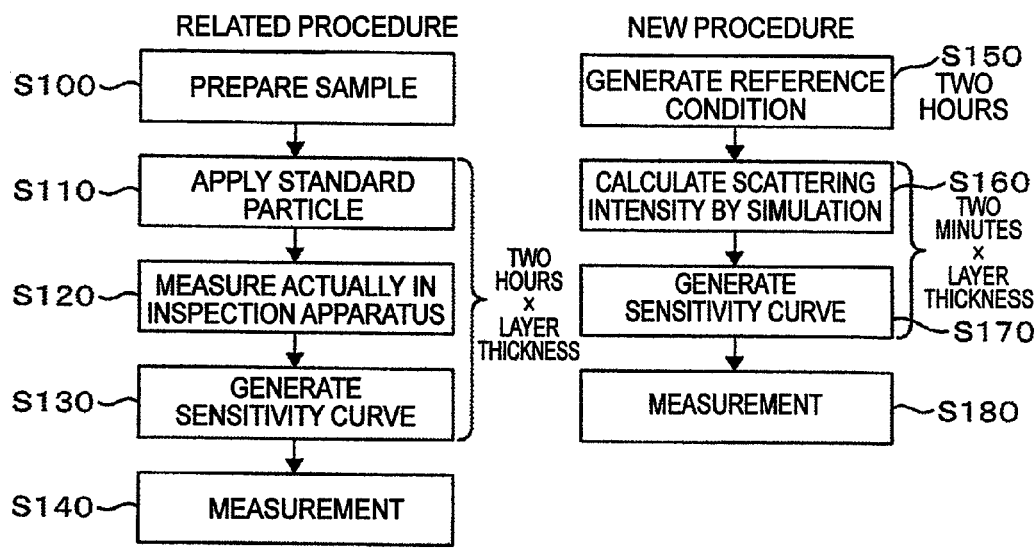
FIG. 18 is a flowchart compared a new procedure with a related procedure.
Figure 19:
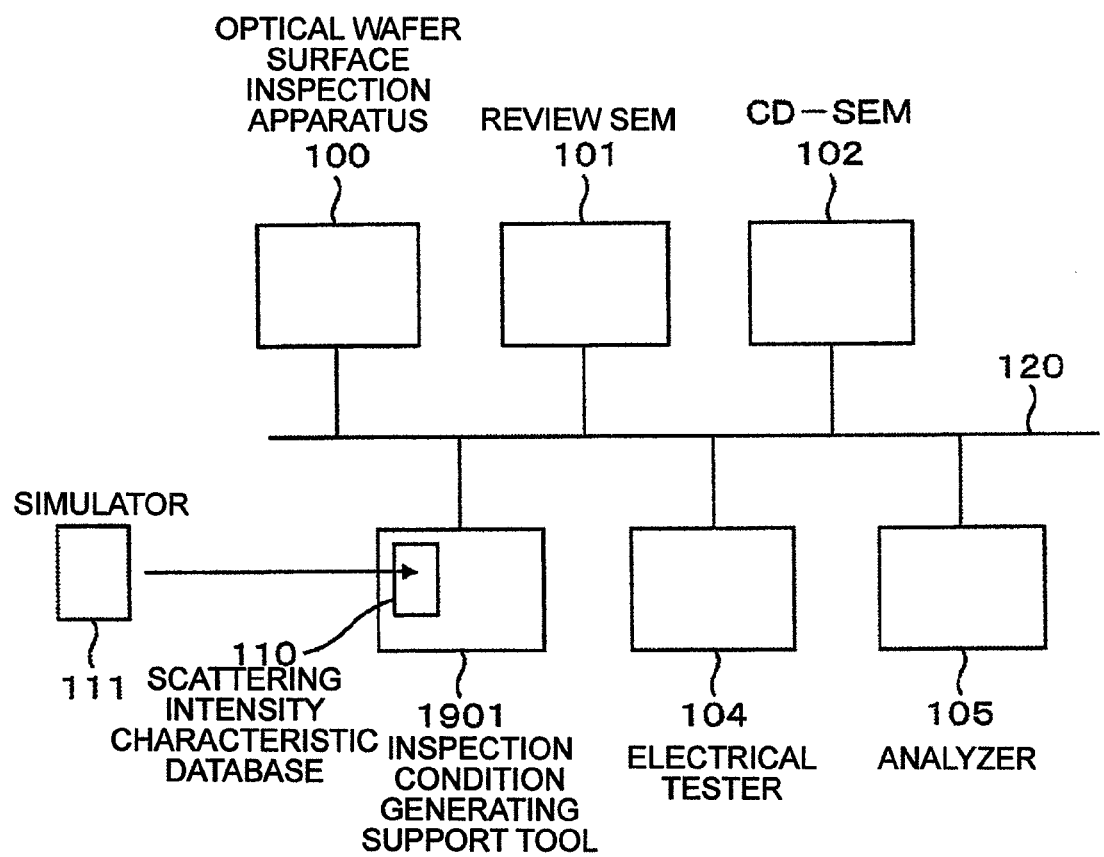
FIG. 19 is a system configuration diagram in a second embodiment.

FIG. 18 is a flowchart showing a comparison between a related procedure and a new procedure in the invention. The related procedure prepares the standard samples for all of the layer thicknesses necessary for the recipe generation at a step S100, and the standard particles of plural sizes are applied to the samples at a step S110. Subsequently, the standard particles of plural sizes are applied to all of the samples to measure by the apparatus at a step S120. In this way, the related procedure requires to prepare the sample for all of the layer thicknesses, measure by the apparatus, make various apparatus parameters optimal, and generate the sensitivity curve from the relation between the particle size and scattering intensity in the sample for all of the layer thicknesses at a step S130. In consequence, the inspection is implemented by using the optimized various apparatus parameters and sensitivity curves. It has taken a "two hours×the number of layer thickness" to operate from the step S110 for applying to the plural standard particles to the step S130 for generating the sensitivity curve. It is required to implement repeatedly the above-mentioned operation by the number of layer types when the layer type is plural.

In the new procedure of the invention, the generation of reference condition operated by the step S130 for generating the sensitivity curve is implemented once for a reference layer thickness at a step S150. In this way, the samples each having different layer thickness can be inspected, at a step S180, by only implementing the generation of sensitivity curve, at a step S170, from the calculation of scattering intensity in the simulation, at a step S160, and the scattering intensity in the simulation, even though the layer thickness of the measured sample is changed. The operation time takes two minutes to calculate the scattering intensity at the step S160 and generate the sensitivity curve at the step S170 from the scattering intensity by the simulation. The operation time necessary for the new procedure is a "two hours+two minutes×number of layer thickness" as a total of the "two hours" necessary for the generation of reference condition and the "two minutes× number of layer thickness" for the operation time of simulation calculation necessary for when the layer thickness is changed. Even by comparing with the "two hours×number of layer thickness" in the related procedure, the operation of applying the standard particles and actual measurement by the apparatus is implemented once for every layer type. Therefore, the operation time can be shortened dramatically, and the cost for spending for the sample can also be cut drastically since the number of sample necessary for the preparation only requires one for every layer type, but requires for the number of layer thicknesses in the related procedure.

FIG. 1 shows an aspect such that the function of the invention is incorporated in the inspection apparatus as a first embodiment, however, a second embodiment is another aspect of an inspection condition generating support tool independent from the function of the invention. The apparatuses and inspection condition generating support tool are coupled with a network 130. The inspection condition generating support tool has the scattering intensity characteristic regarding the layer thickness for every layer type calculated by the simulator 111, and can fetch and add the scattering intensity characteristic thereto, regarding the layer thickness for every layer type calculated separately by the simulator 111. The calculated inspection condition is outputted to transfer to the inspection apparatus 100, so that it is possible to implement a measurement for the sample having the specified layer type and layer thickness.

Further, the following aspects are disclosed in this description, for example.

1. A inspection method of inspecting a defect of a substrate by using a light is that a variation width of a scattering intensity is divided into a plurality of regions as classified by an intensity on the basis of a relation between a layer thickness of a layer formed on the substrate and the scattering intensity.

2. According to the above-mentioned 1, the variation width of the scattering intensity is transformed to a size by using a sensitivity curve (the sensitivity curve acquired from a relation between a particle size and the scattering intensity is sometimes referred to as a calibration curve) calculated from a relation between a particle size and the scattering intensity.

3. According to the above-mentioned 1, the variation width of the scattering intensity is divided into plural numbers on the basis of number of division of either the variation width after divided or the variation width of the scattering intensity.

4. According to the above-mentioned 1, an inspection condition is shared for every divided scattering intensity region to implement an inspection by the shared inspection condition.

5. According to the above-mentioned 1, the inspection method is characterized in that an inspection condition suitable to an inspection targeted substrate is selected from among the inspection requests shared for every divided scattering intensity region to implement an inspection.

6. According to the above-mentioned 1, the inspection method is characterized in that the layer thickness is displayed necessary for generating an inspection condition to be shared for every divided scattering intensity region.

7. An inspection apparatus for inspecting a defect of a substrate by using a light is that it has an optical detector and a control unit for controlling the inspection apparatus on the basis of a detected signal from the optical detector, and the control unit implements a process for dividing a variation width of a scattering intensity into plural regions as classified by the intensity on the basis of a relation between a layer thickness of a layer formed on a substrate and an scattering intensity acquired on the basis of the detected signal.

8. According to the above-mentioned 7, the variation width of the scattering intensity is transformed to a size by using a sensitivity curve (calibration curve) calculated from a relation between a particle size and the scattering intensity.

9. According to the above-mentioned 7, the variation width of the scattering intensity is divided into plural numbers on the basis of number of division of either the variation width after divided or the variation width of the scattering intensity.

10. According to the above-mentioned 7, an inspection condition is shared for every divided scattering intensity region to inspect by a shared inspection condition.

11. According to the above-mentioned 7, an inspection condition suitable to an inspection targeted substrate is selected from among the inspection requests shared for every divided scattering intensity region to implement an inspection.

12. According to the above-mentioned 7, the layer thickness is displayed necessary for generating an inspection condition to be shared for every divided scattering intensity region.

13. According to the above-mentioned 7, an inspection system is configured that it has the inspection apparatus, a database coupled with the inspection apparatus and a simulator coupled to the database.

14. According to the above-mentioned 13, a control unit in the inspection apparatus controls the inspection apparatus on the basis of a signal from the database.

15. An inspection method for inspecting a defect of a substrate by using a light is that it divides a measuring range of a scattering intensity of the light, sets an inspection condition to every divided measuring range, and implements the inspection of the defect by using the inspection condition for every divided measuring range.

16. According to the above-mentioned 15, the inspection condition includes an inspection recipe.

INDUSTRIAL APPLICABILITY

The invention is suitable for use in the inspection/measurement of semiconductor devices and the management of semiconductor manufacturing processes in the field of semiconductor device manufacturers. Further, the configuration of inspection apparatus is not limited to this embodiment, and the inspection target is not limited to the wafer, but may be acceptable to a hard disk substrate etc.

REFERENCE SIGNS LIST 100 optical wafer surface inspection apparatus
101 review SEM
102 CD-SEM
103 data server
104 electrical tester
105 analyzer
111 simulator
120 network
200 wafer
211 sample stage
212 rotation axis
213 rotation drive unit
214 slide drive unit
220 illumination light source
221 illumination light
230 scattering light detecting unit
231$a$ to $d$ detector
232$a$ to $d$ amplifier
233$a$ to $d$ A/D converter
240 signal synthesizing unit
250 entire control unit
260 stage control unit
270 information display unit
280 input operation unit
290 storage unit
310 reference inspection condition inspecting procedure
320 laser power determining procedure
330 polarization condition determining procedure
340 detector sensitivity adjusting procedure
350 sensitivity curve generating procedure
360 detector threshold value setting procedure
370 inspection condition completion
410 sample data display column
411 layer type selecting button
412 layer type display column
413 refractive index display column
414 polarization comparison tab
415 scattering characteristic tab
416 sensitivity curve tab
417 graph setting display column
418 particle size selecting pull-down menu
419 polarization condition selecting check box
420 scattering intensity display range specifying column
421 layer thickness display range specifying column
422 scattering intensity characteristic display column
423 scattering characteristic data
424 polarization condition introductory
510 sample data display column
511 scattering characteristic tab
512 graph setting column
513 polarization condition selecting pull-down menu
514 particle size selecting check box
515 scattering intensity display range specifying column
516 layer thickness display range specifying column
517 scattering intensity characteristic display column
518 particle size introductory
519 scattering characteristic data
610 sensitivity curve tab
611 graph setting column
612 polarization condition selecting pull-down menu
613 layer thickness selecting check box
614 scattering intensity display range specifying column
615 particle size display range specifying column
616 sensitivity curve display column
617 layer thickness introductory
618 sensitivity curve
710 master condition setting column
711 condition storing button
712 condition write-in button
713 condition name entering box
714 layer type selecting pull-down menu
715 particle diameter selecting pull-down menu
716 condition registering button
717 to 712 registration condition selecting pull-down menu
730 region dividing setting column
731 region dividing implementing button 732 automatic region dividing button
733 region dividing method selecting radio button
734 region dividing number entering box
735 size error entering box
736 size error calculated result display box
737 region dividing number calculated result display box
738 scattering intensity divided result
739 scattering intensity characteristic
740 size error range
741 layer thickness applicable range of shared recipe
750 condition generation candidate display column
751 condition generation candidate layer thickness
810 sample specifying column
811 loader selecting button
812 wafer specifying column
821 master condition information display column
822 master condition write-in button
823 master condition name display column
824 layer type display column
825 detection sensitivity selecting pull-down menu
826 region dividing number display column
827 size error display column
831 scattering intensity characteristic display column
832 inspecting wafer display marker
841 inspection start button
842 master condition generating button
901 inspection apparatus using the invention
902 inspection apparatus for inspecting either the inspection apparatus using the invention or substrate after forming pattern
903 network such as Internet
904 server
1011 simulation data
1002 actual measured data
1003 scattering intensity characteristic regarding layer thickness for every layer type
1004 reference layer thickness
1005 scattering intensity regarding particle size
1006 sensitivity curve (simulation)
1007 layer thickness of measuring sample
1008 scattering intensity of the particle sizes for measuring sample
1009 sensitivity curve (actual measurement)
1010 AD value
1011 correspondence table for particle size and AD value
1101 reference recipe information column
1102 sensitivity curve calculation parameter column
1103 sensitivity curve calculated result display column
1104 condition name display column of condition name for reference recipe
1105 layer type name display column
1106 actual measured data name display column
1107 Sim data display column
1108 refractive index (n) entering column
1109 refractive index (k)
1110 low angle AD value correction coefficient entering column
1111 high angle AD value correction coefficient entering column
1112 low angle AD value effective range
1113 high angle AD value effective range
1114 layer thickness entering column
1115 low angle AD value calculated result display column
1116 high angle AD value calculated result
1117 sensitivity curve graph
1118 reference recipe setting button
1119 recipe output button
1201 actual measured data tab
1202 Sim data tab
1203 recipe selecting button
1204 reference recipe (actual measurement) information column
1205 low angle sensitivity curve graph
1206 high angle sensitivity curve graph
1207 OK button
1208 Cancel button
1301 recipe list
1302 recipe holder selecting button
1303 OK button
1304 Cancel button
1401 pull-down menu
1402 pull-down menu
1403 Sim data fetching button
1404 simulation condition display column
1405 low angle scattering intensity characteristic graph
1406 high angle scattering intensity characteristic graph
1407 Sim data list button
1501 pull-down menu
1502 scattering intensity characteristic list regarding layer thickness for every layer type
1503 OK button
1601 inspection condition display column
1602 recipe name entering column
1603 sensitivity curve setting column
1604 CH setting column
1605 inspection condition
1606 recipe name entering column
1607 low angle sensitivity curve name entering column
1608 high angle sensitivity curve entering column
1609 low angle sensitivity curve column
1610 high angle sensitivity curve column
1611 inspection condition updating button
1612 low angle CH setting column
1613 high angle CH setting column
1614 recipe output button
1701 sizes of particle
1702 approximate line-liked straight line
1703 inclination of approximate line-liked straight line

The invention claimed is:
1. An inspection method of inspecting a defect of a substrate, the method comprising:
  a first step which divides a variation width of a scattering intensity into a plurality of regions on the basis of a relationship between a predetermined thickness of a predetermined layer on a predetermined substrate and said scattering intensity by using a processing system;
  a second step which gives an inspection condition to each region by using said processing system;
  a third step which supplies a substrate with light by using an illumination system;
  a fourth step which detects light from said substrate by using a detection system;
  a fifth step which determines a defect of said substrate on the basis of said inspection condition by using said processing system.
2. The inspection method according to claim 1,
  wherein said inspection condition includes at least one of a polarization condition for said illumination system, and a sensitivity curve for acquiring a defect size.
3. The inspection method according to claim 1,
  wherein said first step includes setting a frequency for said dividing or a size error.

4. The inspection method according to claim 1,
wherein said fifth step includes using said inspection condition for a plurality of inspection systems.

5. The inspection method according to claim 1,
wherein said fifth step includes changing said inspection condition as a function of a thickness of a layer on a substrate to be inspected.

6. The inspection method according to claim 1,
wherein said fifth step includes displaying a thickness to be used for said inspection condition in a plurality of inspection systems.

7. An inspection apparatus for inspecting a defect of a substrate, the inspection apparatus comprising:
an optical detector;
a control unit that controls the inspection apparatus in accordance with a detected signal from the optical detector;
an illumination system which supplies a substrate with light; and
a detection system which detects light from the substrate and which includes said optical detector,
wherein the control unit has a processing system which includes a processing unit which divides a variation width of a scattering intensity into a plurality of regions on the basis of a relationship between a predetermined thickness of a predetermined layer on a predetermined substrate and said scattering intensity;
wherein said processing system gives an inspection condition to each region and determines a defect of said substrate on the basis of said inspection condition.

8. The inspection apparatus according to claim 7,
wherein said inspection condition includes at least one of a polarization condition for said illumination system, and a sensitivity curve for acquiring a defect size.

9. The inspection apparatus according to claim 7,
wherein said processing system sets a frequency for dividing said variation width, or a size error.

10. The inspection apparatus according to claim 7,
wherein said inspection apparatus includes a plurality of inspection systems; and
wherein each inspection system uses said inspection condition.

11. The inspection apparatus according to claim 7,
wherein said processing system changes said inspection condition as a function of a thickness of a layer on a substrate to be inspected.

12. The inspection apparatus according to claim 7, further comprising a display system which displays a thickness for said inspection condition to be used in a plurality of inspection systems.

13. The inspection apparatus according to claim 7,
wherein said processing system acquires a scattering intensity corresponding to a predetermined particle size on the basis of simulation data and detection data from said detection system.

14. The inspection apparatus according to claim 7,
wherein said processing system acquires said inspection condition by using a standard inspection condition and a scattering intensity corresponding to a predetermined particle size acquired by using simulation data and detection data from said detection system.

15. The inspection apparatus according to claim 7,
wherein said processing system corrects simulation data by using a refraction index, and acquires a scattering intensity corresponding to a predetermined particle size acquired by using simulation data and detection data from said detection system.

16. The inspection apparatus according to claim 7,
wherein said processing system acquires a correction coefficient by comparing simulation data to a detection data from said detection system, and acquires a scattering intensity corresponding to a predetermined particle size by using a calculation formula with said correction coefficient.

17. The inspection apparatus of claim 7, further comprising:
a database coupled to the inspection apparatus; and
a simulator coupled to said database.

18. The inspection apparatus according to claim 17,
wherein the inspection apparatus operates on the basis of a signal from said database.

* * * * *